United States Patent [19]
Hamaguchi et al.

[11] Patent Number: 5,389,549
[45] Date of Patent: Feb. 14, 1995

[54] METHOD FOR CLASSIFYING LEUKOCYTES AND A REAGENT USED THEREFOR

[75] Inventors: Yukio Hamaguchi, Akashi; Kenji Ito, Kakogawa; Yukio Tsujino, Kobe; Kazuhiro Moriyama, Yokohama; Ikuya Takenaka, Mitaka; Takashi Morikawa; Hitomi Ohmi, both of Akashi, all of Japan

[73] Assignee: Toa Medical Electronics Co., Ltd., Japan

[21] Appl. No.: 964,347

[22] Filed: Oct. 21, 1992

Related U.S. Application Data

[63] Continuation-in-part of Ser. No. 296,085, Jan. 11, 1989, abandoned, and a continuation-in-part of Ser. No. 596,206, Oct. 10, 1990, abandoned.

[30] Foreign Application Priority Data

May 29, 1987 [JP] Japan ................. 62-134433
Mar. 1, 1990 [JP] Japan ................. 2-50814

[51] Int. Cl.⁶ ............................................. G01N 31/00
[52] U.S. Cl. ................................. 436/10; 436/17; 436/18; 436/63; 435/2
[58] Field of Search ................. 436/10, 17, 18, 63; 252/408.1; 435/2

[56] References Cited

U.S. PATENT DOCUMENTS

| | | | |
|---|---|---|---|
| 2,656,508 | 10/1953 | Coulter | 324/71 |
| 3,390,326 | 6/1968 | Imadate | 324/61 |
| 3,502,974 | 3/1970 | Coulter | 324/71 |
| 3,741,875 | 6/1973 | Ansley | 195/103.5 |
| 3,836,849 | 9/1974 | Coulter | 324/71 |
| 4,099,917 | 7/1978 | Kim | 23/230 B |

(List continued on next page.)

FOREIGN PATENT DOCUMENTS

| | | |
|---|---|---|
| 0214614 | 6/1985 | European Pat. Off. . |
| 0177137 | 7/1985 | European Pat. Off. . |
| 0214613 | of 1987 | European Pat. Off. . |
| 0259833 | 9/1987 | European Pat. Off. . |
| 261386 | of 1989 | Japan . |
| 261387 | of 1989 | Japan . |
| 8500868 | 12/1985 | WIPO . |
| 8800762 | 9/1988 | WIPO . |

OTHER PUBLICATIONS

I. Kurokawa, et al. "Experience of the use of Toa Automatic Blood cell counter": *Rinsho Byori* (Clinical Pathology) 16, 251-55, 1968.

(List continued on next page.)

*Primary Examiner*—Nina Bhat
*Attorney, Agent, or Firm*—Pearne, Gordon, McCoy & Granger

[57] ABSTRACT

Reagents for enabling leukocytes to be classified and counted lyse erythrocytes and act on leukocytes to stabilize them are disclosed. The reagents contain polyoxyethylene-based surfactants, and may contain hyperosmotic or hypoosmotic agents and solubilizing agents. One embodiment of the invention contains surfactants selected from the anionic and nonionic polyoxyethylene-based surfactants having 18-30 repeating oxyethylene units per molecule. A second embodiment of the invention contains nonionic polyoxyethylene surfactants only, having 20-100 repeating oxyethylene units per molecule, does not employ either saponin or quaternary ammonium compounds, and provides for adjustment of the pH of the resulting solutions. The invention allows leukocytes to be classified into as many as five types, each type to be quantified, and enables the detection of abnormal cells, when used in conjunction with particulate analysis flow cytometers employing the RF method and the DC method.

26 Claims, 21 Drawing Sheets

U.S. PATENT DOCUMENTS

| | | | |
|---|---|---|---|
| 4,185,964 | 1/1980 | Lancaster | 23/230 B |
| 4,286,963 | 9/1981 | Ledis et al. | 23/230 B |
| 4,485,175 | 11/1984 | Ledis | 436/63 |
| 4,488,175 | 12/1984 | Netravali | 358/136 |
| 4,502,613 | 2/1990 | Chang et al. | 435/2 |
| 4,506,018 | 3/1985 | North, Jr. | 436/10 |
| 4,528,274 | 7/1985 | Carter et al. | 436/10 |
| 4,529,705 | 7/1985 | Larsen | 436/17 |
| 4,617,275 | 10/1986 | Matsuda et al. | 436/10 |
| 4,637,986 | 1/1987 | Brown et al. | 436/10 |
| 4,745,071 | 5/1988 | Lapicola et al. | 436/63 |
| 4,751,179 | 7/1988 | Ledis et al. | 435/34 |
| 4,962,038 | 10/1990 | Carter et al. | 436/10 |
| 5,116,539 | 5/1992 | Hamaguchi et al. | 252/408.1 |

OTHER PUBLICATIONS

I. Kurokawa, et al. *Rinsho Kensa* (Clinical Testing) 11, 148–151. 1967.

K. Shintani, "Problems with Leukocyte counting", *Rensho Kensa,* (Clinical Testing) 12, 900–905, 1968.

Hamaguchi, et al., *Chemical Abstracts* CA 111:228524v (Dec. 1989) abstract of WO 09504 PCT/JP88/00514, priority doc U.S. #07/926,085.

Y. Takamori, et al. "On Factors Causing Variations in Leukocyte Size-Frequency Distribution and Their Effects on Leukocyte Counts" *MCC News,* 34, Dec. 21, 1969.

Helleman, P. W., et al. *Scand. J. Haematology,* 6, 160–165, 1969.

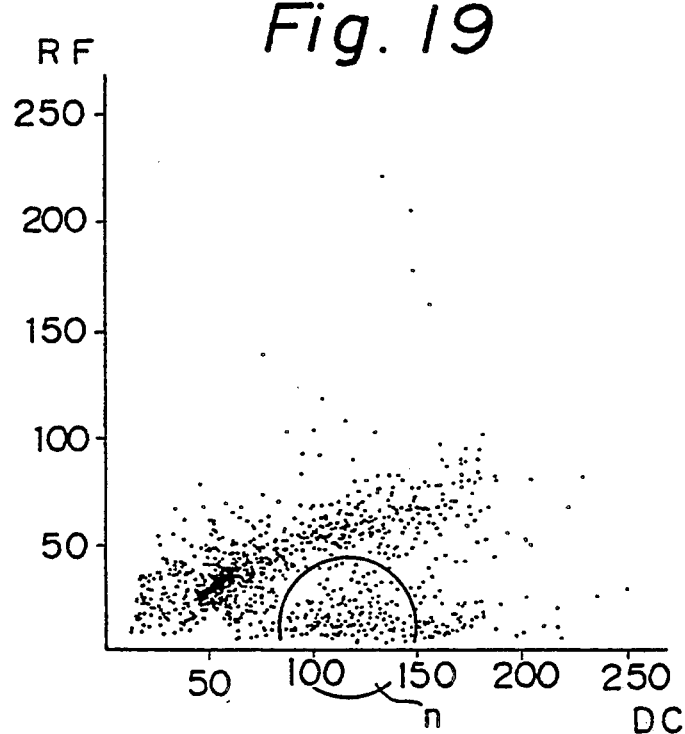
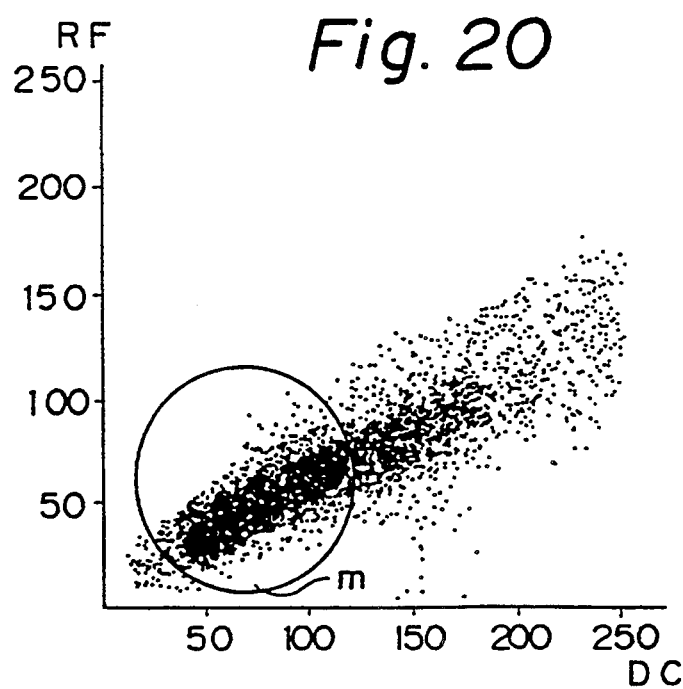

METHOD FOR CLASSIFYING LEUKOCYTES AND A REAGENT USED THEREFOR

This application is a continuation in part of U.S. Ser. No. 07/296,085, filed Jan. 11, 1989, and copending U.S. Ser. No. 07/596,206, filed Oct. 10, 1990, the parent applications being combined herein.

TECHNICAL FIELD

The present invention relates to a method of classifying and measuring blood corpuscles in the area of clinical testing. More particularly, the present invention relates to a method of and reagents for classifying, differentiating and counting leukocytes in blood.

BACKGROUND ART

Leukocytes in the peripheral blood of normal subjects consist of five types, i.e., lymphocytes, monocytes, neutrophils, eosinophils and basophils. The latter three kinds of leukocytes are collectively referred to as granulocytes. Different leukocyte types have different functions and counting of leukocytes in the blood according to their type provides valuable information for diagnostic purposes. For instance, an increase in the number of neutrophils is associated with such diseases as inflammations, myocardial infarction and leukemia, and a decrease in their number is associated with viral diseases, hypoplastic anemia, agranulocytosis, etc. On the other hand, an increase in the number of eosinophils is found in such diseases as parasitosis, Hodgkin's disease and allergosis. An increased number of monocytes occurs either during the convalescence period of patients suffering from infections diseases or in such diseases as monocytic leukemia.

In addition to the above-mentioned lymphocytes, monocytes, neutrophils, eosinophils and basophils which are generally referred to as "normal cells", abnormal cells occasionally appear in the peripheral blood of patients suffering from certain hemodyscrasias. For instance, gemmules or blasts are sometimes found in the peripheral blood of leukemia patients. Such abnormal cells also occur in various types and classifying them and determining the number of cells in each class of abnormal cells is also of great importance in clinical fields.

The classification and counting of leukocytes has most commonly been conducted by the differential counting method which is also referred to as the visual counting method, or simply as the manual technique.

In this method, a blood sample is smeared on a glass plate and the blood corpuscles in the smear are stained for examination by microscopy. The technician identifies the type of individual leukocytes according to their morphological features (e.g., their size, the morphology of their nucleus and cytoplasm, and the presence or absence of granules) or the degree of dye uptake and performs classification and counting of them. At ordinary laboratories, 100-200 leukocytes are usually counted for each sample and the percentage of the total leukocyte count occupied by each type of corpuscle is recorded as a measured value.

The differential counting method has several disadvantages. First, microscopic observation must be preceded by cumbersome procedures for preparing a specimen that involve such steps as smearing a blood sample on a glass plate, fixing the corpuscles and staining them. Secondly, it is a great burden for the technician to identify subtle differences between corpuscles by microscopic classification and counting. Thirdly, it is difficult even for a skilled technician to yield consistent counts by the manual method since, aside from the small number of leukocytes computed, the smeared sample often has an uneven distribution of blood corpuscles.

Under these circumstances, there has arisen a strong need for a method to be developed that is capable of automated classification and counting of leukocytes. The automated techniques so far realized may be roughly divided into two types.

The first method consists of recording the images of corpuscles with a video camera or some other suitable imaging device classifying the leukocytes by means of image processing on a computer. The operating principles of this method are similar to those of the conventional visual counting method but primarily due to the existence of many corpuscles that defy classification by processing with a computer, this method has not yet become an ideal alternative to the manual method. Another problem with this method is that it requires sophisticated equipment which is bulky and costly.

The other approach toward automatic classification and counting of leukocytes is based on a flow system. In this method, a blood sample having corpuscles suspended in a diluent is permitted to flow in such a way that the corpuscles will individually (one by one) pass through a constricted detector and leukocyte classification is conducted by analyzing the signals generated by the detector. This second method which makes use of a flow system is further subdivided into two categories.

In a method of the first category, an electrolyte in which all red cells present are disrupted with a lysing agent so that only leukocytes will be suspended is permitted to flow through an orifice and the change in electrical impedance that occurs at the orifice when each corpuscle passes through it is detected, the magnitude of the detected signal being used as a basis for classification of leukocytes.

A method of the second category is characterized by the use of a flow cytometer that comprises a light source, a flow cell that permits the blood cells in a sample to flow one by one through a constricted channel, a photometric unit that detects light issuing from each blood cell, and an analyzer for analyzing the detected signal. In this method, the corpuscles in the sample which are stained are illuminated under light and the fluorescence emitted from the irradiated corpuscles is detected, optionally together with scattered light, with leukocyte classification being conducted in accordance with the intensity of the detected signal.

This method of the second category has problems in practical use such as the need to adopt a complicated staining process, as well as the use of sophisticated and costly equipment including an optical system.

One of the principles underlying the method of the first category is disclosed in Japanese Patent No. 508,789 and U.S. Pat. No. 3,390,326. According to this principle, a sample prepared by suspending particles in a fluid medium having a different dielectric constant is allowed to pass through a fluid channel having a constricted portion held between closely adjacent electrodes and the change that occurs in the electric impedance between the electrodes on account of the difference in dielectric constant between the particles and the fluid medium is detected.

A description of a practical apparatus that operates on this principle may be found in Ichiro Kurokawa et al., "Toa jidokekkyukeisuki no shiyoukeiken (Experience of the Use of Toa Automatic Blood Cell Counter)" in "Rinsho Byori (Clinical Pathology)", vol 16 pp 251–255, 1968. This apparatus has a 3.5 MHz high-frequency oscillator which applies a high-frequency current to the detector circuit, and the change in electric impedance that occurs between the electrodes in the detector circuit as corpuscles in suspension pass through the detector circuit is detected.

A description of leukocyte measurements with a Toa Automatic Blood Cell Counter may be found in Ichiro Kurokawa et al., "Rinsho Kensa (Clinical Testing)" vol. 11, pp. 148–151, 1967. The described method consists of adding saponin to a suspension of blood cells so that the erythrocytes are lysed to enable the measurement of leukocytes that are left intact.

Besides saponin, there are several other lysing agents available that are capable of lysing erythrocytes. Among such blood lysing agents, CTAC (cetyltrimethyl ammonium chloride) and Tergitol monionic NPX display a strong lytic activity under use conditions but, at the same time, the protoplasm of leukocytes is also attacked and their nuclei will become almost naked. In contrast, saponin allows leukocytes to remain fairly close to their intact state. Therefore, CTAC and Tergitol monionic NPX are unsuitable for use as blood lysing agents in a model such as Toa Automatic Red Cell Counter that detects the change in electric impedance at high frequencies (see Kazuo Shintani, "Hakekkyusantei no mondaiten (Problems with Leukocyte Counting)" in "Rinsho Kensa (Clinical Testing)" vol 12, pp 900–905, 1968.

In determining the number of leukocytes with an automatic blood cell counter, it is necessary that the magnitude of signals from leukocytes be sufficiently large compared to the signals of dissolved erythrocyte membranes (ghosts) and attendant noise to enable clear differentiation between the two kinds of signals. In order to determine whether this condition is established, a cumulative size-frequency distribution curve as shown in FIG. 15 is often used. The graph shown in FIG. 15 is constructed by plotting the signal threshold values of an automatic blood cell counter on the horizontal axis, and the number of detected signals exceeding a certain signal threshold value on the vertical axis. In FIG. 15, portion A is generally referred to as "a flat portion" of the cumulative size-frequency distribution curve, and in order to ensure that leukocyte signals being measured are sufficiently larger than the abovementioned noise and ghost signals to yield consistent leukocyte counts, the equipment and reagents used therewith must be adjusted so as to allow the flat portion A to be extended.

In practice, however, it has been pointed out that measurements of leukocytes with a Toa Automatic Blood Cell Counter using saponin as a blood lysing agent produce a shorter "flat portion" than when the DC method to be described later in this specification is employed. For instance, the graph in FIG. 15 was constructed from the data in Table 1 given in Yuji Takamori et al., "Hakekkyuryudobunpu no hendoyoin to sono keisuchi ni oyobosu eikyo ni tsuite (On Factors Causing Variations in Leukocyte Size-Frequency Distribution and Their Effects on Leukocyte Counts)" in MCC News, No. 34, pp. 12–21, Toa Tokushu Denki Hyogo, Japan, 1969 (the data shows the cumulative size-frequency distribution obtained with saponin added to samples left for 5 minutes after dilution), and the flat portion of the curve in this graph extends only from the threshold value of 350 to 400.

As for the shortness of the flat portion obtained when leukocyte measurements are conducted with a Toa Automatic Red Cell Counter using saponin, P. W. Helleman, et al., Scand. J. Haematology, 6 pp. 160–165, 1969, comments that this phenomenon would be due to the difference in dielectric properties between dissimilar types of leukocytes (as between a lymphocyte and a granulocyte).

A careful review of the cumulative size-frequency distribution curve in FIG. 15 will show that it contains a second flat portion B on the right side of the first flat portion A. This fact will become clearer if one constructs a size-frequency distribution curve as shown in FIG. 16 by plotting the number of leukocytes for each threshold level as calculated from the cumulative size-frequency distribution curve in FIG. 15. Stated more specifically, FIG. 16 contains the population of erythrocyte ghosts and noise which is indicated by C, the first population of leukocytes indicated by D which lies rightward of C, and the second population of leukocytes indicated by E which is situated rightward of D. It is therefore possible to say that the division of the leukocyte size-frequency distribution into two populations has produced short flat portions in the cumulative size-frequency distribution.

The foregoing discussion amounts to a showing of the fact that two different populations of leukocytes have to date been classified and counted by the Toa Automatic Blood Cell Counter and that the above-described method of detecting the change in electric impedance at high frequency (This method is hereinafter referred as the RF method) has the potential to count leukocytes after classifying and differentiating them into several types.

However, at the time when the Toa Automatic Blood Cell Counter was developed and commercialized, the primary concern was to obtain leukocyte counts in a consistent and reliable manner and no detailed investigation was conducted to unravel the reason for the shortness of flat potions of a cumulative size-frequency distribution curve. On the contrary, most efforts were directed at adjusting the equipment and reagents in such a way that the flat portions could be extended as much as possible to ensure consistent counting of leukocytes.

Besides the RF method described above, the principle underlying the method of the first category which is included in the scope of the methods making use of a flow system is also described in Japanese Patent No. 217,947 and U.S. Pat. No. 2,656,508. According to this principle, a sample having particles suspended in a fluid medium having a different conductivity is allowed to pass through a narrow current channel and any change in current that occurs on account of the difference in conductivity between the particles and the fluid medium is detected. This method is hereunder referred to as the DC method. In the DC method, the magnitude of a signal detected is substantially proportional to the volume of particles.

When this DC method is combined with the already-described RF method, information on the volume of particles is obtained by the DC method and, in addition to that, information derived from the structure of the particles and the properties of the constituent materials of the particles can be obtained. An apparatus that relies on this approach for classifying several populations of different types of particles from a system comprising a mixture of different types of particles in the same suspension is disclosed in Japanese Patent No. 785,859 and U.S. Pat. No. 3,502,974. However, these patents show nothing about the possibility of classifying and counting different populations of leukocytes.

The already-described RF method may be modified in such a way that, instead of disrupting corpuscles, their contents are replaced so that their dielectric constant is changed, followed by classification and counting procedures. A method based On this approach is disclosed in Japanese Patent No. 936,823 and U.S. Pat. No. 3,836,849. In the second example of these patents, 250 $\mu$l of a 1% saponin solution is added to 100 $\mu$l of whole blood suspended in a phosphate buffered physiological saline solution having a pH of 7.2, and then the erythrocytes are lysed and two distinct peaks for leukocytes appear. This result agrees well with that obtained by performing measurements with a Toa Automatic Blood Cell Counter (FIG. 16).

Even if the RF method is performed using saponin which produces a comparatively mild action on corpuscles, the protoplasm of leukocytes is slowly disrupted to cause gradual attenuation of signals from leukocytes. If one wants to replace the contents of corpuscles at normal pH's without disrupting them as in Japanese Patent No. 936,823, it is necessary to reduce the concentration of saponin to a significantly low level so that it will act slowly on leukocytes. However, in this case, the preliminary treatment for starting a measurement takes quite a long time as compared to the time of the preliminary treatment necessary for ordinary leukocyte measurements (3–5 minutes), so it is not suitable for practical purposes to use this method with automatic analyzers which have to process many specimens in a short period of time.

A different approach that brings about a change in leukocytes in a fairly short period of time and which classifies the leukocytes into three populations on the basis of the amount of that change has been realized using the DC method and is described in National Publication of Translated Version No. 500097/1985 and U.S. Pat. No. 4,485,175.

In this method, a quaternary ammonium salt which is also described in Japanese Patent No..936,823 is used as a cytolytic agent and by using it at low concentration, a change in the volume of leukocytes is produced and the leukocytes are classified into three populations on the basis of this difference. However, the results of an example given in U.S. Pat. No. 4,485,175 are as shown in FIG. 17 and lymphocytes, monocytes and granulocytes in the three populations of leukocytes are not necessarily completely separated or differentiated.

Furthermore, the quaternary ammonium salt, even if it is used at low concentration, has such a great effect on corpuscles that hemolysis will take place within a short period of time. According to Japanese Patent No. 936,823, only the dielectric constants of corpuscles are changed without replacing or disrupting their contents, but in the absence of any specific data, it is not clear whether this is actually possible.

Considering the fact that quaternary ammonium salts cause an undesirably high degree of damage to leukocytes that are to be classified and counted, National Publication of Translated Version No. 502277/1986 and International Publication No. WO85/05684 propose a method in which mildly acting saponin is added at high concentration and its lysing action is quenched at the time when the erythrocytes have been lysed and only thereafter is analysis performed with a flow cytometer or by the combination of the Rf and DC methods.

This method requires a fixing agent in order to quench the lysing action and, furthermore, a special procedure such as adding it at a predetermined timing and thereafter heating the cells at elevated temperatures must be taken. This method is therefore not very effective for use with automatic analyzers.

As described above, among the methods that automatically classify and count leukocytes using a flow system, the method of the second category which makes use of flow cytometer has a disadvantage in that the equipment is sophisticated and expensive. As for the method of the first category which detects that change in impedance that occurs at an orifice when corpuscles pass through the orifice, and wherein leukocytes are classified in accordance with the magnitude of detected signals, certain problems also arise depending on whether leukocytes are changed mildly or violently: in the former case, it takes as much time to complete the preliminary treatments or a special fixing agent must be added at a predetermined timing or subsequent heat treatment is necessary; in the latter case, leukocytes are damaged so extensively that they cannot be classified into more than three types. Therefore, none of the methods of the second category that have so far been proposed are satisfactory for practical purposes. As for the method of the first category, no technique has ever existed that is capable of classifying and counting abnormal cells such as the already-described blasts by utilizing this method.

Furthermore, saponin as a cytolytic agent to be used in the method of the first category is labile in terms of blood lysing action whereas quaternary ammonium salts are too violent as noted above.

According to the first embodiment of the present invention, neither saponin nor quaternary ammonium salts are used as cytolytic agents, and instead a cytolytic agent having consistent lysing action is used to lyse erythrocytes and damage leukocytes in a very short period of time. Thereafter, analysis is made by the combination of the already-described DC and RF methods, thereby providing remarkable advantages, such as classification of normal cells into five types as well as classification of abnormal cells, which have been unattainable in the prior art techniques of leukocyte classification.

On the other hand, Japanese Patent Public Disclosure No. 134957/88 (EP Patent Publication No. 259833) discloses a process for classifying leukocytes (a method of the second category) comprising hemolyzing erythrocytes in a first solution which is acidic and hypoosmotic, neutralizing the acidity of the first solution and adjusting the osmolarity by using a second solution, and measuring leukocytes by a flow cytometer to classify them. Moreover, Patent Domestic Announcement No. 502931/89 (PCT/US88/00762) discloses a process (a method of the first category) for classifying leukocytes comprising lysing erythrocytes in a first solution which is acidic and hypoosmotic, neutralizing the acidity of the first solution and adjusting the osmolarity by using a second solution, and classifying and counting leukocytes by using the RF and DC methods in combination.

However, ghosts due to erythrocytes (hereinafter referred to as "erythrocyte ghosts") cannot be sufficiently reduced only by hemolyzing erythrocytes in an acidic and hypoosmotic as conducted in the above two methods. Therefore when measuring leukocytes by using RF and DC methods, said ghosts and the intensity of the detected signs partially overlap and as a result, cannot be definitely distinguished. Since either of these two methods requires a reagent consisting of two solutions, an automatic blood analyzer wherein such methods are practiced necessarily becomes complicated.

Incidentally, although it is described in a reference [Clinical Analysis (Rinshō Kensa) Book, Additional Volume 1, "Pretreatment for Examination of Samples", page 3 published by Kanahara Shuppan] that a smear must be prepared within 4 hours after blood gathering, smears are often prepared many hours after blood gathering in a big institution such as a clinical examination center. In such cases, injury of leukocytes increases as time passes and particularly neutrophils and monocytes are remarkably injured. Therefore, results of the classification of leukocytes obtained from blood gathered 24 hours previously are largely different from those of leukocytes obtained immediately after blood gathering.

Therefore there has been a need for a method for accurately classifying leukocytes in blood gathered many hours earlier.

The object of the second embodiment of this invention is to provide a process wherein neither saponin nor quaternary ammonium is used as a cytolytic agent but another cytolytic agent exhibiting stable hemolytic activities is used to hemolyze erythrocytes and to stabilize leukocytes in a short time, wherein erythrocyte ghosts can be distinguished from lymphocytes and normal leukocytes are classified into five types and abnormal cells are classified, and wherein accurate values of the classified leukocytes can be obtained for blood gathered many hours earlier.

DISCLOSURE OF INVENTION

In order to solve the aforementioned problems of the prior art and to realize certain remarkable advantages, the first embodiment of the present invention provides reagents and methods for classifying leukocytes as set forth below.

A reagent for classifying leukocytes that lyses erythrocytes and which acts on leukocytes to enable the classification and counting of leukocytes, said reagent containing at least one surfactant selected from the group consisting of:

(a) a surfactant of a first group which is a polyoxyethylene-based anionic surfactant represented by the formula:

$R_1$-$R_2$-$(CH_2CH_2O)_n$-X where $R_1$ is an alkyl, alkenyl or alkynyl group having 10–22 carbon atoms;

$R_2$ is O,

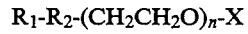

or COO;

n is an integer of 8–30;

X is $SO_3Na$, COONa, $OSO_3Na$ or ONa; and (b) a surfactant of a second group which is a polyoxyethylene-based nonionic surfactant represented by the formula:

$R_1$-$R_2$-$(CH_2CH_2O)_n$-H where $R_1$ is an alkyl, alkenyl or alkynyl group having 10–22 carbon atoms;

$R_2$ is O,

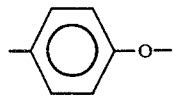

or COO;

n is an integer of 8–30. This reagent may also contain a hyperosmotic agent.

A reagent for classifying leukocytes which is composed of the following two fluids (a) and (b):

(a) a first fluid which is a blood diluent and which contains a hyperosmotic agent; and (b) a second fluid that contains the reagent set forth in 1 and which is to be added to a blood sample that has been diluted with the first fluid.

This reagent may also contain a surfactant in the first fluid.

The reagents described above may also contain a solubilizing agent that selectively reduces the size of monocytes in leukocytes.

The solubilizing agent agent is at least one member selected from the group consisting of the following solubilizing agents:

urea
thiourea
1,1-dimethylurea
ethyleneurea
methylurethane
1,3-dimethylurea
urethane ($H_2NCOOC_2H_5$)
N-octyl B-D-glucoside
CHAPS (3-[(3-chloroamidopropyl)dimethylammonio]-1-propanesulfonate)
CHAPSO (3-[(3-chloroamidopropyl) dimethylammonio]-2-hydroxy-1-propanesulfonate)
MEGA 8,9,10 (octanoyl-, nonanoyl- or decanoyl-N-methylglucamide)
sucrose monocaprate
N-formylmethylleucylalanine
guanidine thiocyanate
guanylguanidine
guanidine chloride
guanidine rhodanate
guanidine nitrate
1,1,3,3-tetraguanidine
guanidine carbonate
guanidine phosphate
guanidine sulfate
sodium deoxycholate
taurocholic acid
cholic acid
sodium trichloroacetate
sodium tribromoacetate
sodium dichloroacetate
sodium dibromoacetate
sodium monochloroacetate
sodium monobromoacetate.

A method of classifying leukocytes into three types, lymphocytes, monocytes and granulocytes, by the RF and DC particle analyzing methods using a reagent for classifying leukocytes that lyses erythrocytes and which acts on leukocytes to enable the classification and counting of leukocytes, said reagent containing at least one surfactant selected from the group consisting of:
(a) a surfactant of a first group which is a polyoxyethylene-based anionic surfactant represented by the formula:
R₁-R₂-(CH₂CH₂O)ₙ-X
where
R₁ is an alkyl, alkenyl or alkynyl group having 10–22 carbon atoms;
R₂ is O,

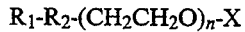

or COO;
n is an integer of 8–30;
X is SO₃Na, COONa, OSO₃Na or ONa; and
(b) a surfactant of a second group which is a polyoxyethylene-based nonionic surfactant represented by the formula:
R₁-R₂-(CH₂CH₂O)ₙ-H
where
R₁ is an alkyl, alkenyl or alkynyl group having 10–22 carbon atoms;
R₂ is O,

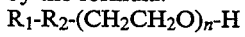

or COO;
n is an integer of 8–30.

A method of classifying leukocytes into four types, lymphocytes, monocytes, eosinophils and granulocytes other than eosinophils, which comprises classifying the leukocytes into three types, lymphocytes, monocytes and granulocytes, by the method set forth above, and counting by both the RF and DC methods or by the DC method alone the eosinophils that selectively remain intact after the passage of a predetermined period of time in the sample to be measured that has been used for classification into three types.

A method of classifying leukocytes into four types, lymphocytes, monocytes, eosinophils and granulocytes other than eosinophils, which comprises classifying the leukocytes into three types, lymphocytes, monocytes and granulocytes, by the method set forth in above, while counting by both the RF and DC methods or by the DC method alone the eosinophils that are selectively left intact by using any of the reagents set forth above.

A method of classifying leukocytes into five types, lymphocytes, monocytes, eosinophils, basophils and neutrophils, which comprises classifying the leukocytes into four types, lymphocytes, monocytes, eosinophils and granulocytes other than eosinophils, by the methods described above, while counting basophils by both the RF and DC methods or by the DC method alone using a reagent for the measurement of basophils which selectively leaves basophils intact.

A method of detecting abnormal cells by the RF and DC particle analyzing methods using a reagent set forth above.

A method of classifying leukocytes into three types, lymphocytes, monocytes and granulocytes, and detecting abnormal cells by the RF and DC particle analyzing methods using the reagent set forth above.

A method of classifying leukocytes using a reagent that contains at least one of the solubilizing agents of the second group:
n-octyl-B-D-glucoside
CHAPS (3-[(3-chloramidopropyl)dimethylammonio]-1-propanesulfonate)
CHAPSO (3-[(3-chloramidopropyl)dimethylammonio]-2-hydroxy-1-propanesulfonate)
MEGA 8, 9, 10 (octanoyl-, nonanoyl- or decanoyl-N-methylglucamide)
sucrose monocaprate
N-formylmethylleucylalanine The additional problems associated with erythrocytes mentioned above can be solved by using the reagent of the second embodiment of this invention and the process for classifying leukocytes of the second embodiment of this invention wherein the reagents set forth below are used.

These reagents and processes are as shown in the following:

A reagent for enabling leukocytes to be classified and measured by lysing erythrocytes and acting on leukocytes, which has a pH of 1.5–5.0, and an osmolarity of 10–120 mOsm/kg and contains a polyoxyethylene based nonionic surfactant represented by the formula:
R₁-R₂-(CH₂CH₂O)ₙ-H
where
R₁ is an alkyl, alkenyl or alkynyl group having 12–22 carbon atoms;
R₂ is —O—,

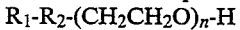

or —COO—; and
n is an integer of 20–100;
said reagent being substantially free of either saponin or quaternary ammonium compounds.

This reagent may be comprised of a first solution which is a reagent for classifying leukocytes that lyses erythrocytes and which acts on leukocytes to enable the classification and counting of leukocytes, said reagent containing at least one surfactant selected from the group consisting of:
(a) a surfactant of a first group which is a polyoxyethylene-based anionic surfactant represented by the formula:
R₁-R₂-(CH₂CH₂O)ₙ-X
where
R₁ is an alkyl, alkenyl or alkynyl group having 10–22 carbon atoms;
R₂ is O,

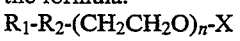

or COO;
n is an integer of 8–30;
X is SO₃Na, COONa, OSO₃Na or ONa; and (b) a surfactant of a second group which is a polyoxyethylene-based nonionic surfactant represented by the formula:

$R_1\text{-}R_2\text{-}(CH_2CH_2O)_n\text{-}H$ where $R_1$ is an alkyl, alkenyl or alkynyl group having 10-22 carbon atoms;

$R_2$ is O,

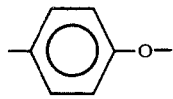

or COO;

n is an integer of 8-30 and a second solution to be added to the first solution, and is a pH of 5.0-12.0 and has an osmolarity of 150-2000 mOsm/kg after addition of the second solution to the first solution, and is substantially free of either saponin or quaternary ammonium compounds.

The second solution may contain a polyoxyethylene based nonionic surfactant represented by the formula:

$R_2\text{-}R_2\text{-}(CH_2CH_2O)_n\text{-}H$ where $R_1$ is an alkyl, alkenyl or alkynyl group having 12-22 carbon atoms;

$R_2$ is —O—,

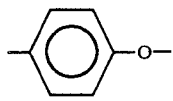

or —COO—; and n is an integer of 20-100.

The cytolytic solution contains at least one solubilizing agent selected from the group consisting of:

urea
thiourea
1,1-dimethylurea
ethyleneurea
methylurethane
1,3-dimethylurea
urethane ($H_2NCOOC_2H_5$)
N-octyl B-D-glucoside
CHAPS (3-[(3-chloroamidopropyl) dimethylammonio]-1-propanesulfonate)
CHAPSO (3-[(3-chloroamidopropyl) dimethylammonio]-2-hydroxy-1-propanesulfonate)
MEGA 8,9,10 (octanoyl-, nonanoyl- or decanoyl-N-methylglucamide)
sucrose monocaprate
N-formylmethylleucylalanine
guanidine thiocyanate
guanylguanidine
guanidine chloride
guanidine rhodanate
guanidine nitrate
1,1,3,3-tetraguanidine
guanidine carbonate
guanidine phosphate
guanidine sulfate
sodium deoxycholate
taurocholic acid
cholic acid
sodium trichloroacetate
sodium tribromoacetate
sodium dichloroacetate
sodium dibromoacetate
sodium monochloroacetate
sodium monobromoacetate.

A method for classifying leukocytes into at least three types, including lymphocytes, monocytes and granulocytes, by using a reagent of the second embodiment and particulate analysis methods consisting of RF method and DC method.

A method for detecting abnormal cells by using a reagent of the second embodiment and particulate analysis methods consisting of RF method and DC method.

By using the reagents of the first embodiment of the present invention for classifying leukocytes, the erythrocytes in blood are lysed and the leukocyte species are individually damaged. When the so treated sample is subjected to a measurement by the combination of the RF and DC methods, the leukocytes are separated into three populations of lymphocytes, monocytes and granulocytes in accordance with the difference in speed at which the cell volume changes depending upon the amount of damage sustained by individual leukocytes. In accordance with the present invention, two-dimensional information is obtained by the RF and DC methods and the reagents of the present invention have characteristic actions; because of these features, the present invention enables leukocytes to be classified into three types in a more efficient and reliable way than the method described in U.S. Pat. No. 4,485,175 which uses a quaternary ammonium salt as a cytolytic agent and which classifies leukocytes into three types by the DC method alone.

If the reagents for leukocyte classification of the first embodiment of the present invention are used and a measurement made by the combination of the RF and DC methods, the leukocytes are separated into four populations of lymphocytes, monocytes, eosinophils and granulocytes other than eosinophils in accordance with the difference in speed at which the cell column changes in dependence upon the amount of damage sustained by individual leukocytes. In this case, the RF and DC methods may be combined in various ways, and one effective way is that the leukocytes are first classified into three types, lymphocytes, monocytes and granulocytes, by the RF and DC methods, and then the eosinophils that selectively remain intact after the passage of a predetermined period of time are counted by both the RF and DC methods or by the DC method alone.

In another variation of the first embodiment, the leukocytes are classified into four types by the method described above, while at the same time, the basophils are selectively left intact using a reagent for the measurement of basophils and the sample obtained is subjected to measurement by both the RF and DC methods or by the DC method alone. As a result of these procedures, the numbers of eosinophils and basophils are calculated, so the number of neutrophils left in the granulocytes can be determined by subtracting the numbers of eosinophils and basophils from the total count of granulocytes. In this way, the leukocytes can be classified into five types, with the respective number of lymphocytes, monocytes, neutrophils, eosinophils and basophils in the leukocytes as well as their percentages being established.

The methods of the present invention, unlike the method described in National Publication of Translated Version No. 502277/1986, have no need to use a labile lytic agent, saponin, nor do they require treatment with a special fixing agent or heat treatment at elevated temperatures; therefore, these methods find particular advantages in use with automatic analyzers.

The characteristic actions of the reagents for leukocyte classification of the present invention are described below.

The surfactant of the first group contained in the reagents of the first embodiment of the present invention is an anionic surfactant, and the surfactant of the second group is a nonionic surfactant. In general application, anionic and nonionic surfactants are both used extensively as detergents, emulsifiers, dispersants and penetrants in various industrial fields including textiles, laundry, synthetic resins, printing inks, metals, photography, foodstuffs and pharmaceuticals.

In contrast, the quaternary ammonium salt used as a cytolytic agent in methods such as the one described in U.S. Pat. No. 4,488,175 is a cationic surfactant. In the general applications of cationic surfactants, properties based on their surface activity such as wetting property, detergency and ability to lower surface tension are rarely applied directly, and they are extensively and chiefly used as bactericides, disinfectants, water-proofing agents, softening agents, antistats and sealing agents in such industrial fields as textiles, rubbers, plastics, pharmaceuticals, civil engineering, ceramics and petroleum.

Saponin has often been used as a cytolytic agent and unlike the above-described anionic, nonionic and cationic synthetic surfactants, saponin is a natural chemical substance of plant origin, the chemical structure and properties of which will vary from one production lot to another.

As such, these cytolytic agents have different chemical properties and different origins, so they naturally cause different actions on leukocytes.

Of the cytolytic agents listed above, saponin is the mildest in its action on cells whereas the quaternary ammonium salt damages cells most violently. In comparison, the strength of the action of anionic and nonionic surfactants on cells would be intermediate between saponin and the quaternary ammonium salt.

A comparison of the amounts of cell damage caused by different cytolytic agents is given in Table 1 below in terms of the size of lymphocytes. The figures in the table are approximate values.

TABLE 1

| Damage to Lymphocytes | |
| --- | --- |
| Before treatment | 170–250 fl |
| After treatment with saponin | 100–120 fl |
| After treatment with the surfactants of the present invention | 70–80 fl |
| After treatment with quaternary ammonium salt | 50 fl |

As shown above, the quaternary ammonium salt causes an undesirably high degree of damage to leukocytes and hence is not considered to be a preferred lysing agent for the purpose of leukocyte classification. FIG. 14 shows the results of a leukocyte measurement by the RF and DC methods using a quaternary ammonium salt. Obviously, the leukocytes are not separated into a plurality of populations. This is because the leukocytes are damaged so extensively by the quaternary ammonium salt that they lose almost all of the cytoplasm, though their cell membrane is left intact; as a result, the difference in the intensity of signals detected from various leukocyte species is not so great as to be clearly differentiated by the RF and DC methods to produce separate fractions on a two-dimensional distribution diagram.

Thus, it is entirely meaningless to use a quaternary ammonium salt as a cytolytic agent in a method of classifying leukocytes by the combination of the Rf and DC methods. On the other hand, saponin acts only mildly on leukocytes and suffers the already-described disadvantage that it takes a prolonged time to complete preliminary treatments. Furthermore, the ability of saponin to lyse blood is not consistent.

The surfactants of the first and second groups to be used in the present invention do not damage leukocytes as violently as quaternary ammonium salts but act more strongly on leukocytes than saponin and will damage the individual leukocytes to an extent that is very favorable for the purpose of leukocyte classification.

FIG. 9 shows the results of fractionating leukocytes by performing RF and DC measurements on a blood sample before addition of a cytolytic agent. Obviously, granulocytes a are clearly separated from monocytes b but lymphocytes c and erythrocytes i are not. Furthermore, this diagram shows the strong effects caused by simultaneous passage of erythrocytes. The described classification and counting of leukocytes are therefore impossible unless some modification is made.

However, even if no cytolytic agent is added, a sample in which only the leukocytes have been carefully separated permits the leukocytes to be fractionated to some extend through measurements by the RF and DC methods. The results of fractionation by this approach are shown in FIG. 10.

Fractions were obtained by separating the leukocytes in blood through centrifugation by identifying differences in specific gravity using Percoll-Hypaque, and the obtained fractions were subjected to measurement. Some portion of the erythrocytes is left unseparated in the sample. As FIG. 10 shows, granulocytes a, monocytes b and lymphocytes c can be separated without using a cytolytic agent. However, separating only leukocytes as in the case described above is very difficult and time-consuming even for a skilled operator, and in addition to that, this work cannot be automated. In practice, therefore, the method in which the erythrocytes are lysed to leave only leukocytes intact has to be adopted. However, if a cytolytic agent is added to lyse erythrocytes, the leukocytes are also subjected to the action of that agent. Hence, it is necessary to ensure that even after the erythrocytes have been lysed, granulocytes, monocytes and lymphocytes are sufficiently separated to come out clearly on a two-dimensional distribution diagram. FIG. 11 shows the results of an experiment in which a cytolytic agent which was the same as what is used in Example 2 to be described later in this specification was added to a blood sample which was also the same as the blood employed in the operation of separating only leukocytes, and in which the leukocytes were classified through measurements by the RF and DC methods for a period of 5 seconds following elapse of 14 seconds from the addition of the lytic agent. The scale of FIG. 11 is the same as that of FIG. 10. One can readily see that the leukocytes decreased in overall size after the addition of the lytic agent. It is also interesting to note that the speed at which monocytes decrease in volume is particularly high and that the monocytes which produced stronger DC signals than granulocytes before the addition of the lytic agent yielded weaker signals after the addition of the agent. FIG. 2 showing the results of Example 2 to be described herein is drawn on an enlarged scale compared to FIG. 11. FIGS. 10 and 2 differ in scale with respect to both the DC and RF methods. Stated more specifically, after the addition of a lysing agent, the cells decrease in size, and the signals detected also become weak. In FIG. 2, the signals detected are amplified for the sake of clarity (so are the results of the examples to be described herein).

The methods of the present invention lyse erythrocytes and damage individual leukocytes by means of the reagents of the present invention and classifying and count leukocytes in accordance with the difference in speed at which the cells change in volume in dependence upon the amount of damage sustained by the leukocytes. In addition, the present invention which employs a cytolytic agent does not have to rely upon centrifugation of the type described above.

We have so far described the ability of the reagents of the present invention to enable classification and counting of normal leukocyte cells. Surprisingly enough, the present inventors have also found that if erythrocytes are lysed using the reagents of the present invention and when leukocytes are measured by the DC and RF methods, not only the normal leukocyte cells described above but also various types of abnormal cells can be classified and counted. FIG. 18 is a diagram showing the positions at which various types of abnormal cells appear. The distribution diagram shown in FIG. 18 was obtained by measuring the blood of a healthy person using the reagents of the present invention, and the dots in this diagram represent the values obtained from normal cells. If any population of abnormal cells is to be found, it will appear in the vicinity of one of the regions surrounded by the solid lines. Among the abnormal cells to be detected, the population of left-shift cells will essentially appear in region j, immature granulocytes (IG) in region k, blasts in region l, heterolymphocytes in region m, lymphoblasts in region n, nucleated erythrocytes in region o, and platelet agglutinating cells in region p. Neutrophils consist of segmented cells and band cells and the more juvenile the cells are, the less segmented their nuclei are and band nuclei will predominate. The increase in the number of juvenile cells, or band cells, in leukocytes is called a "left shift". Left-shift cells, immature granulocytes and blasts are normal leukocytes that are in the state of immaturity or juvenility, and their juvenility increases in the order written. It is generally held that the more immature the leukocytes are, the smaller their specific gravity and the smaller the intensity of signals that are produced by the RF method. Therefore, the most juvenile blasts appear in the lowest part of FIG. 18. The platelet agglutinating cells appear when platelets aggregate for some reason to glow to a size comparable to leukocytes, and it is important to differentiate and eliminate these cells if one wants to obtain correct leukocyte counts.

There is no prior art technique that has ever succeeded in classifying and counting abnormal leukocyte cells by either the DC or RF methods or combination thereof. A method has been proposed for detecting abnormal leukocyte cells by optical principles of measurement (see Japanese Patent Public Disclosure No. 88896/1986) but as already pointed out, detection by the disclosed optical principles of measurement requires sophisticated equipment and very complicated procedures. Furthermore, according to the disclosure in the above identified patent, the nuclei of all leukocytes except basophils become naked. Therefore, the method as described therein is capable of detecting abnormal cells and basophils but is unable to classify and count normal leukocytes other than basophils. A need therefore arises for the provision of a separate measuring channel in order to allow for classification and counting of normal leukocyte cells. It was not until the development of the methods and reagents of the first embodiment of the present invention that simultaneous classification and counting of both normal and abnormal leukocyte cells became possible.

Prior art techniques in which reagents containing polyoxyethylene-based surfactants are used for the purpose of leukocyte classification include the methods described in Japanese Patent Public Disclosure No. 22891/1979 and U.S. Pat. No. 4,409,917 as well as the method described in Japanese Patent Public disclosure No. 71857/1987 (corresponding to European Patent Publication No. 214,613). All of these methods are within the scope of the method of the second category which employs a flow system as already described herein under the section of "Prior Art" and they utilize an optical apparatus for measurement. Since these methods employ a completely different principle of measurement than the methods of the present invention, needless to say the reagents disclosed in the above-mentioned patents cannot be directly applied to the methods of the present invention whose operating principle is detection of impedance. In addition, according to the experiments conducted by the present inventor, some of the polyoxyethylene-based surfactants disclosed in those prior patents are not only unsuitable for use in the methods of the present invention for leukocyte classification but also lack the ability to dissolve erythrocytes. On the contrary, certain polyoxyethylene-based surfactants are used as sheath solutions for blood cell counting apparatus that are essential for the protection of erythrocytes (see Japanese Patent Public Disclosure No. 87233/1987, and Japanese Patent Application Nos. 261386/1987 and 261387/1987).

As will be understood from the above explanation, there are many polyoxyethylene-based surfactants that have no ability to dissolve erythrocytes and those which are suitable as compositions to be incorporated in the reagents of the present invention for leukocyte classification are even more limited in number.

The present inventors performed screening on a great number of anionic and nonionic surfactants including polyoxyethylene-based surfactants and found as a result that the surfactants of the first and second groups set forth in claims 1 and 5 are suitable for the purposes of the present invention.

The objects of the first embodiment the present invention can be attained if the carbon number of $R_1$ in the general formula set forth in claims 1 and 5 is 10–22 and if n (the number of added moles) is 8–30. For better fractionation of leukocytes, the carbon number of $R_1$ is preferably 12–18, with n being 12–15.

When fresh blood that has just been sampled is measured using the reagent set forth in claims 1 and 5 (this reagent is hereinafter referred to as a lysing reagent), lymphocytes, monocytes and granulocytes can be fractionated in a desired way. However, if blood, especially abnormal blood, is left to stand for several hours, say 8 hours, after sampling, a two-dimensional distribution as shown in FIG. 12 is obtained. Regions a, b and c in FIG.

12 denote those regions where granulocytes, monocytes and lymphocytes are respectively found when normal blood that has just been sampled is measured. An abnormal increase is observed in the number of cells in normal region b for monocytes, and lymphocytes c and monocytes b are poorly fractionated, with a decrease in the number of granulocytes a. This is because as time goes by after blood sampling, leukocyte cells in abnormal blood become brittle and highly sensitive to the action of the lysing reagent added, causing granulocytes, in particular part of the cells of neutrophils, to decrease in volume more rapidly than when they do right after blood sampling. Another reason is that the lysing reagent acts on the blood so abruptly that it will not act uniformly on individual corpuscles (the corpuscles are not dispersed uniformly in the solution of lysing reagent) but rather act strongly on some corpuscles in preference over others.

These problems could be partly solved by merely diluting the blood before the addition of the lysing reagent using a common diluting solution for achieving uniform dispersion of corpuscles. However, the present inventors figured out certain reagents that were capable of allowing leukocytes to be classified and counted in a very consistent way even when blood was left to stand for several to several tens of hours after sampling.

The reagent set forth in the claims is composed of two fluids. The first fluid is a so-called liquid diluent and contains a hyperosmotic agent. The second fluid is the lysing reagent. Blood is first diluted and the corpuscles dispersed uniformly with the first fluid which is a liquid diluent. Then, the second fluid which is a lysing reagent is added to dissolve the erythrocytes and to allow the leukocytes to be classified and counted.

The hyperosmotic agent present in the first fluid adjusts the osmotic pressure of the first fluid to 285 mOsm or above. A method in which a solution for leukocyte measurement is processed into a hypertonic solution (hyperosmotic solution) is described in Japanese Patent Public Disclosure No. 71857/1987, but as already mentioned, optical principles of measurement are adopted in the invention described in this patent and the action and the effect of the hypertonic solution employed in it are entirely different from those of the first fluid which is rendered hypertonic in the present invention. According to said patent, lymphocytes become circular saw-toothed blood cells by the action of the hypertonic solution on corpuscles and this contributes to improved discrimination between detection signals for lymphocytes and noise. In the absence of any detailed description in this patent, it is not clear why the change to circular saw-toothed blood cells contributes to the improved ability to distinguish from noise, but it would be some reason that is closely related to the principles of optical measurement. According to the principles of impedance measurement employed in the present invention, information about the size or interior of cells is detected by the DC or RF method and deformations of the contour of cells will essentially result in no effect on the intensity of signals detected. The purpose of rendering hyperosmotic the first fluid in the present invention is as follows: by placing corpuscles under high osmotic pressure, the Cell membranes of corpuscles are dehydrated so as to become rigid enough to be protected against the violent shock that would otherwise occur when the second fluid which is a lysing reagent is subsequently added. Besides this protecting effect, placing corpuscles under high osmotic pressure causes the shrinkage of cell membranes, thereby allowing the corpuscles to decrease in volume. As already mentioned, information on the size of cells is to be detected according to the principles of impedance detection, so if the volume of corpuscles is excessively reduced, it becomes difficult to distinguish them from noise. For this reason, placing corpuscles under high osmotic pressure has generally been avoided in leukocyte measurements according to the principles of impedance detection. Quite surprisingly, however, the present inventors found that even when the second fluid which is a lysing reagent was allowed to act after the corpuscles had been placed under high osmotic pressure by treatment with the first fluid, leukocyte signals could be distinguished from noise as clearly as when the lysing agent was allowed to act on the blood from the beginning. This would be because the cell membranes of leukocytes were protected by the action of the first fluid. In this way, the reagent composed of two fluids, the first one of which was a hyperosmotic fluid, allowed leukocyte cells to be protected from the violent shock that would be caused by the second fluid, which was a lysing reagent, and yet the reagent assured satisfactory discrimination of leukocyte signals from noise. This enabled leukocytes to be classified and counted in a consistent way without permitting neutrophils to get into the region of monocytes in the above-described two-dimensional distribution diagram even when a measurement was conducted on blood that had been left to stand for several tens of hours after sampling. FIG. 13 shows the results of an experiment in which blood that was the same as what was employed to obtain the results shown in FIG. 12 was measured with the above-described two-component reagent system when it had been left to stand for 8 hours after sampling as in the case shown in FIG. 12. Obviously, granulocytes a, monocytes b and lymphocytes c were clearly fractionated without any abnormal increase in the number of cells in the region of monocytes. It should be mentioned here that the osmotic pressure of the first fluid must be at least about 285 mOsm. Below, this value, the membranes of leukocytes will not be fully protected. Hyperosmotic agents that can be used with advantage include ethylene glycol and alcohols.

Ideally, the reagent of the first embodiment of the present invention is composed of two fluids, with the first fluid being made a hyperosmotic solution. On the other hand, the two-component system is not desirable since its use complicates the procedure of analysis or the composition of analyzing equipment. Therefore, a one-component reagent system in which the lysing reagent is formulated as a hyperosmotic fluid has been figured out. This reagent is not capable of protecting the membranes of corpuscles as completely as the two-component system but the present inventor confirmed that even this one-component reagent system had the capability to allow leukocytes to be classified and counted consistently at practically satisfactory levels without permitting neutrophils to get into the region of monocytes in the above-described two-dimensional distribution diagram even when a measurement was conducted on blood that had been left to stand for several tens of hours after sampling.

Whether the reagent is of a two-component or one-component system, it is more effective for a fixing agent to be incorporated in the hyperosmotic fluid. This fixing agent serves to assist in the leukocyte cell membrane protecting action of the hyperosmotic fluid. Prior art techniques that perform leukocyte classification using reagents that contain a fixing agent are described not only in the aforementioned Japanese Patent Public Disclosure Nos. 22891/1979 and 71857/1987 and National Publication of Translated Version No. 502277/1986 but also in U.S. Pat. No. 3,741,875. In all of these prior art techniques, the solution has to heat-treated after the addition of a fixing agent. In contrast, there is no need to perform a heat treatment even after the addition of the reagent containing a fixing agent. In all of the prior art techniques mentioned above, the fixing agent is responsible for the important part of the action to be displayed by the reaction reagent, so there is a particular need to promote the reaction of the fixing agent by performing a heat treatment. On the other hand, the fixing agent in the reagent of the present invention plays only an auxiliary role and there is no particular need to promote the reaction by performing a heat treatment. This absence of the need for heat treatment offers a great benefit which can be enjoyed by simplifying the method of apparatus of analysis.

In the first embodiment of the present invention, at least one solubilizing agent may be incorporated and this is also effective for the purpose of improving the precision of leukocyte classification. Solubilizing agents generally serve to dissolve slightly water-soluble or completely water-insoluble substances to an extent that apparently exceeds their solubility and are extensively used in industrial and biological fields. In medical fields, solubilizing agents are used to make water-soluble drugs from vitamins and hormones. However, the solubilizing agents employed in the present invention have activities that are different from the general functions described above. Monocytes in leukocytes have inherently strong reactivity with lysing reagents containing surfactants and they are the cells that decrease in volume most rapidly after the addition of lysing reagents. However, the present inventors found that when a solubilizing agent was incorporated in the lysing reagent or in the liquid diluent that was to be used before the lysing regent, the solubilizing agent promoted the action of the lysing reagent on monocytes, thereby causing them to decrease in volume even more rapidly. In other words, the solubilizing agents used in the present invention act selectively on monocytes. It was also found that these solubilizing agents which acted selectively on monocytes were effective not only for the reagents characteristic of the present invention that contained a surfactant which was selected from the group consisting of the aforementioned surfactants of the first and second groups, but also for all reagents for leukocyte classification that could be learned from the prior art. Among these solubilizing agents, those set forth above are particularly effective.

A surfactant can also be incorporated in the first fluid (the liquid diluent rendered hyperosmotic) in the already-described two-component reagent system. The surfactant to be used in this case may be selected from among the surfactants of the first and second group set forth above or alteratively they may be common surfactants. The principal activity of the surfactants to be contained in the first fluid is not to dissolve corpuscles but is closer to the activity of the solubilizing agents described above. In other words, the osmotic pressure of the first fluid is high enough to weaken the lysing action of the surfactants in it and they would serve to perform a preliminary treatment for selectively promoting the shrinkage of monocytes among the corpuscles which are to be lysed as a result of the subsequent addition of the lysing reagent. It is therefor required that the surfactant in the second fluid has a substantially stronger cytolytic activity than the surfactant in the first fluid. Otherwise, the dissolving reaction of corpuscle cells will not proceed even if the second fluid is added. If the first fluid has a higher osmotic pressure than the second fluid, the condition noted above is satisfied even if the surfactants contained in the first and second fluids are of the same kind and have the same concentration.

All of the reagents described above in the first embodiment of the present invention contain a buffer agent for adjusting the solution to a predetermined pH. At pH's below the predetermined value, the lysing reaction is retarded and the state where the leukocytes can be classified will not be reached within the requisite time for practical purposes. At pH's above the predetermined value, the lysing reaction is so greatly accelerated that it becomes difficult to classify the leukocytes in a stable state.

Although not characteristic of the present invention, common antioxidants or electroconductive adjusting agents may be incorporated, as required, in all of the reagents of the present invention.

It is well known that erythrocytes are hemolyzed in a hypoosmotic solution but the process of the second embodiment of this invention is characterized in that erythrocytes can be hemolyzed under hypoosmotic (10–120 mOsm/kg) and acidic conditions in a solution containing a nonionic surfactant.

If the solution is neutralized, damage to leukocytes becomes more severe and erythrocyte ghosts do not sufficiently decrease. On the other hand, if the solution is made alkaline, damage to leukocytes becomes very severe. Therefore, it is essential to hemolyze erythrocytes under acidic conditions, as described in the second embodiment of the present invention. Erythrocyte ghosts cannot be decreased only when the acidic and hypoosmotic conditions are combined.

BRIEF DESCRIPTION OF DRAWINGS

The attached drawings may be explained as follows.

in FIG. 15, A and B signify flat portions of the cumulative size-frequency distribution curve.

FIG. 19 is a two-dimensional distribution diagram as obtained in the measurement of blood from a patient with acute lymphocytic leukemia (ALL).

FIG. 20 is a two-dimensional distribution diagram as obtained in the measurement of blood from a patient with adult T-cell leukemia (ATL).

In FIGS. 1 to 14, and 26-33, symbols a through i have the following meanings:
  a: granulocytes
  b: monocytes
  c: lymphocytes
  d: eosinophils
  e: basophils
  f: erythrocyte ghosts
  g: leukocytes other than eosinophils
  h: leukocytes other than basophils
  i: erythrocytes.

In FIGS. 18 to 33, symbols j through p have the following meanings:
  j: left shifts
  k: immature granulocytes (IG)
  l: blasts
  m: heterolymphocytes
  n: lymphoblasts
  o: nucleated erythrocytes p: platelet aggregation
q: leukemia cells For the description of RF and DC in FIGS. 2–14 and 18–33, see the relevant explanation of FIG. 1.

BEST MODES FOR CARRYING OUT THE INVENTION

EXAMPLE 1

The following is an example in which Sandet EN [the trade name of Sanyo Chemical Industries, Ltd. for the chemical formula: $C_{12}H_{25}$—O—$(CH_2CH_2O)_2SO_3Na$], one kind of surfactant from among those in the first group, was used as a cytolytic agent.

Figure 1:
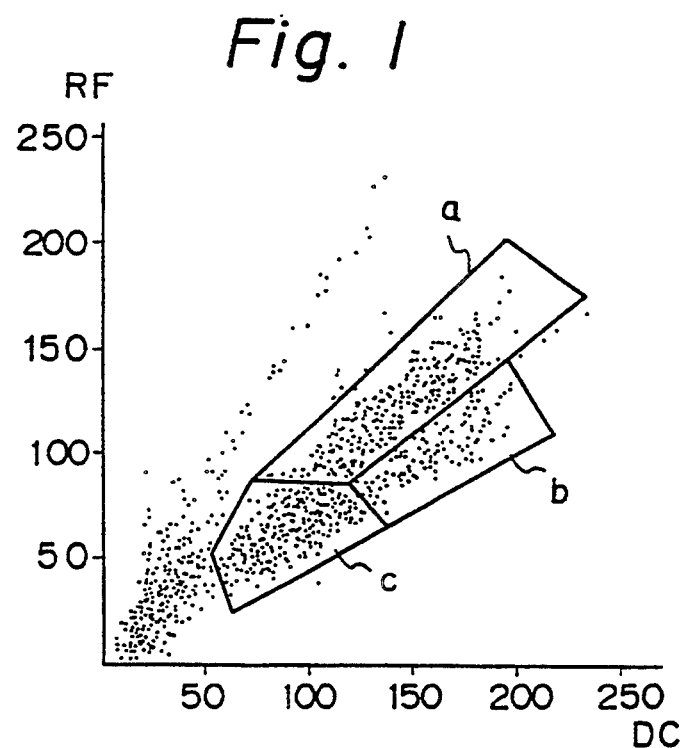
FIG. 1 is a two-dimensional distribution diagram showing the results of classification of leukocytes in Example 1; the horizontal axis of this two-dimensional distribution diagram plots the relative intensity of signals as obtained when the measurement was conducted by the DC method and the vertical axis plots the relative intensity of signals as obtained when the measurement was conducted by the RF method; the dots in FIG. 1 represent the cells that produced DC and RF signals of the intensities of which are respectively associated with the DC and RF methods; and DC and RF in FIG. 1 represent the intensities of DC and RF signals, respectively.

Blood (60 μl) was diluted with 5 ml of a 0.125% solution of said cytolytic agent and 10 ml of a liquid diluent consisting of 1/60M phosphate buffer agent and 0.6% sodium chloride, and measurement was started 14 seconds after the addition of the cytolytic agent under the following conditions: pH, 7.0; osmotic pressure, 120 mOsm; and solution temperature, 26° C. The results of leukocyte measurement conducted for 5 seconds are shown in FIG. 1. The horizontal axis of the two-dimensional distribution diagram shown in FIG. 1 plots the relative intensity of signals as obtained when the measurement was conducted by the DC method, and the vertical axis of FIG. 1 plots the relative intensity of signals as obtained when the measurement was conducted by the RF method. The dots in FIG. 1 represent cells that produced DC and RF signals the intensities of which are respectively associated with the DC and RF methods.

Figure 17:
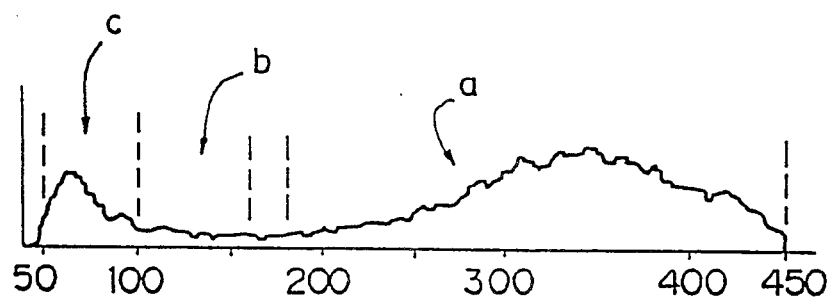
FIG. 17 is the leukocyte size-frequency distribution curve obtained by performing the DC method as described in an example of U.S. Pat. No. 4,485,175.
Figure 18:
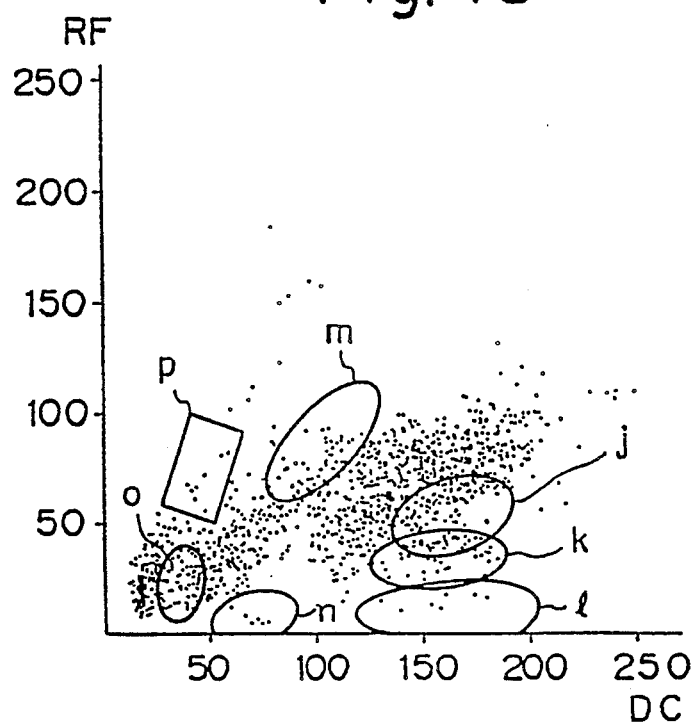
FIG. 18 is a diagram showing the positions at which various types of abnormal cells appear in a two-dimensional distribution diagram.

As FIG. 1 shows, the leukocytes were fractionated into populations that could be presumed to consist of lymphocytes, monocytes and granulocytes, respectively. Since the measurement was conducted by a combination of the RF and DC methods to construct a two-dimensional distribution diagram, the leukocytes could be fractionated more clearly than when they were classified into three types by using the DC method alone, as in the prior art, the results of which are shown in FIG. 17.

EXAMPLE 2

Measurements were conducted under the same conditions as those employed in Example 1 except that 4.0% conc. Emulmin 140 [the trade name of Sanyo Chemical Industries, Ltd.; containing 56% $C_{18}H_{37}$—O—$(CH_2CH_2O)_{14}H$, 34% $C_{16}H_{33}$—O—$(CH_2CH_2O)_{14}H$, and 7% $C_{14}H_{29}$—O—$(CH_2CH_2O)_{14}H$] and 0.5% conc. Emulgen 420 [the trade name of Kao Corp. for $C_{18}H_{14}$—O—$(CH_2CH_2O)_{13}H$] were used. The results are shown in FIG. 2.

As in Example 1, the leukocytes were classified into three populations. The fact that these populations consisted of lymphocytes, monocytes and granulocytes, respectively, was confirmed by analyzing the samples containing the individually separated leukocyte species and by performing a correlation test with the visual counting method.

Figure 2:
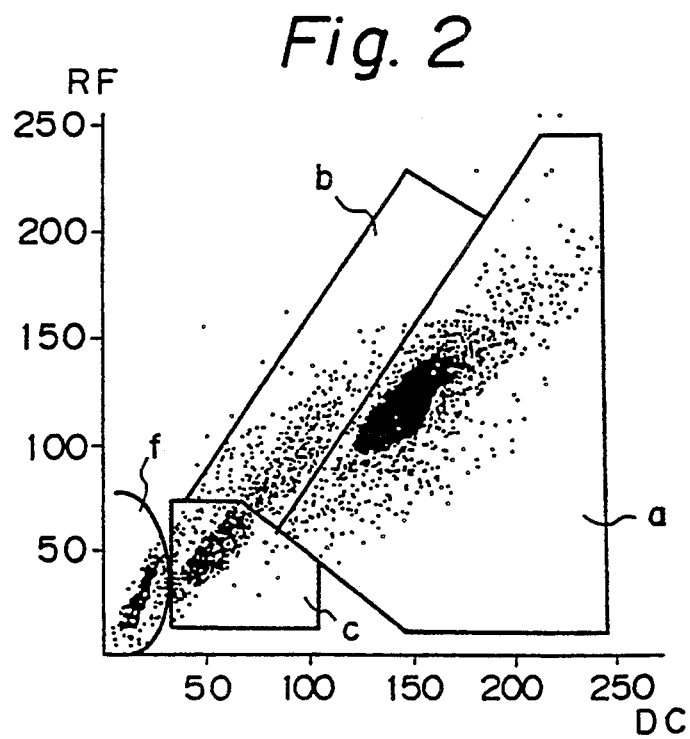
FIG. 2 is a two-dimensional distribution diagram showing the results of classification of leukocytes in Example 2; for the description of this diagram, see the relevant explanation of FIG. 1.

Comparing FIG. 2 with FIG. 1, one will be able to see that the position of the appearance of monocytes relative to granulocytes is different. This is because the speed at which the individual leukocytes change in volume differs depending upon the kind and concentration of lysing agent. In FIG. 2, monocytes which are inherently larger than granulocytes appear at smaller positions (smaller intensities of DC signals) than granulocytes because the monocytes were damaged at a notably higher speed than the other leukocytes.

Figure 3:
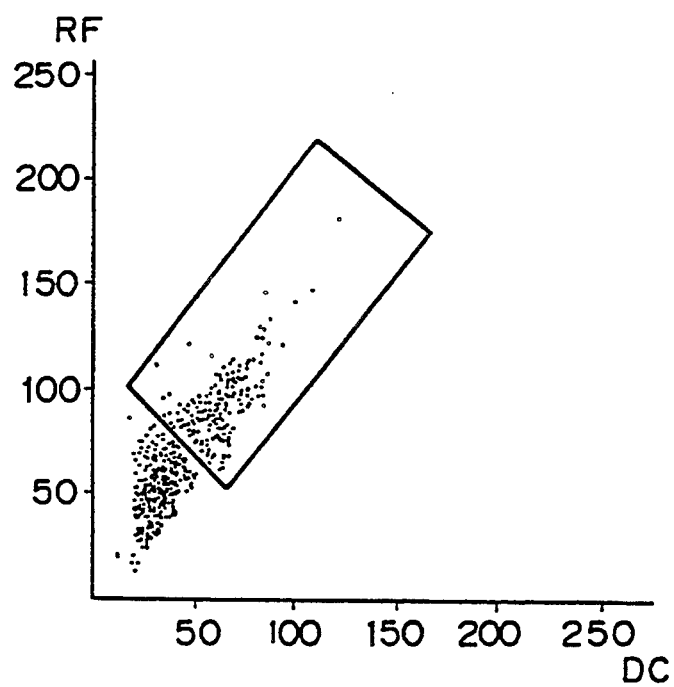
FIG. 3 is a two-dimensional distribution diagram showing the results of leukocyte classification conducted as in the case of FIG. 2 except that the blood sample was left to stand for 90 seconds after the addition of a lysing agent.
Figure 4:
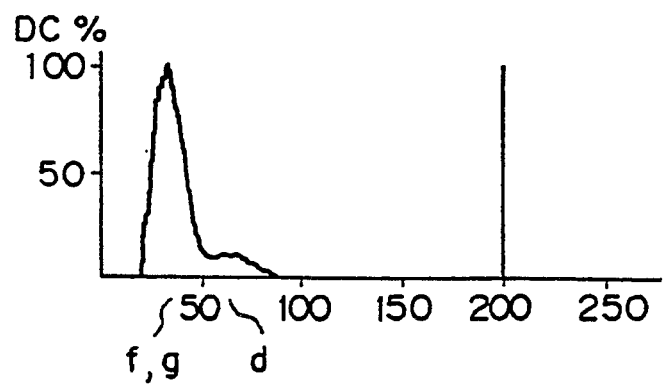
FIG. 4 is a graph showing the results of leukocyte classification conducted by the DC method alone in Example 2 under the same conditions as those employed in obtaining the data shown in FIG. 3.

Except for the use of the cytolytic agent described above, a blood-containing liquid diluent was prepared in the same manner as in Example 1, and this sample was left to stand for 90 seconds after the addition of the lysing agent. A measurement was conducted during the subsequent 5 seconds. The results are shown in FIG. 3. The present inventors found in this measurement that only eosinophils were left intact and could be selectively detected as separate entities from the other leukocytes. This could be explained by the high resistance of the membranes of eosinophils against the lysing agent employed. When the measurement was conducted by the DC method alone under the same conditions, the results shown in FIG. 4 were obtained, from which one can see that eosinophils were satisfactorily separated from the other leukocytes.

EXAMPLE 3

A measurement was conducted for 5 seconds following the passage of 13 seconds after the addition of the lysing agent under the same conditions as those employed in Example 2, except that the pH was adjusted to 10.0. In this case, too, eosinophils were successfully separated from the other leukocytes as in Example 2.

In the three examples shown above, the concentration of the lysing agents was adjusted to 0.125% or 4.5%. Similar results will be obtained of the concentration of lysing agents is within the range of 0.01–15%, preferably 0.05–10%. The. pH was adjusted to 7.0 or 10.0 but satisfactory results can be obtained if it is within the range of 4.0–12.0, preferably 7.0–10.0. The osmotic pressure was held at 120 mOsm, but good results can be obtained if it is within the range of 50–400 mOsm, preferably 100–200 mOsm. The solution temperature was 26° C., but equally good results can be obtained in the measurement if it is within the temperature range of 10°–37° C. It should, however, be noted that the time at which a measurement is started following the addition of lysing agents must be adjusted depending upon the temperature.

The composition of the liquid diluent containing a buffer and other ingredients, as well as the concentration of such ingredients, are in no way limited to the examples shown above. In the above example, the cytolytic agent and the liquid diluent were prepared as separate solutions, but they may be preliminarily mixed to prepare a single lysing fluid.

EXAMPLE 4

In the three examples described above, basophils in the granulocytes were not separated. In order to separate and count basophils, the following procedures may be taken.

Blood (80 μl) was diluted with 10 ml of a reagent for basophil measurement containing 1.44% conc. Emulgen 123-P [the trade name of Kao Corp. for the chemical formula: $(C_{12}H_{25}$—O—$(CH_2CH_2$—O—$)_{23}H]$, 0.435% conc. potassium ophthalate, 0.025% conc. hydrochloric acid and 0.025% conc. nitric acid, and measurement was conducted for 5 seconds following the lapse of 13 seconds after the addition of the lysing agent under the following conditions: pH, 3.0; osmotic pressure, 60 mOsm; and solution temperature, 33° C.

Figure 5:
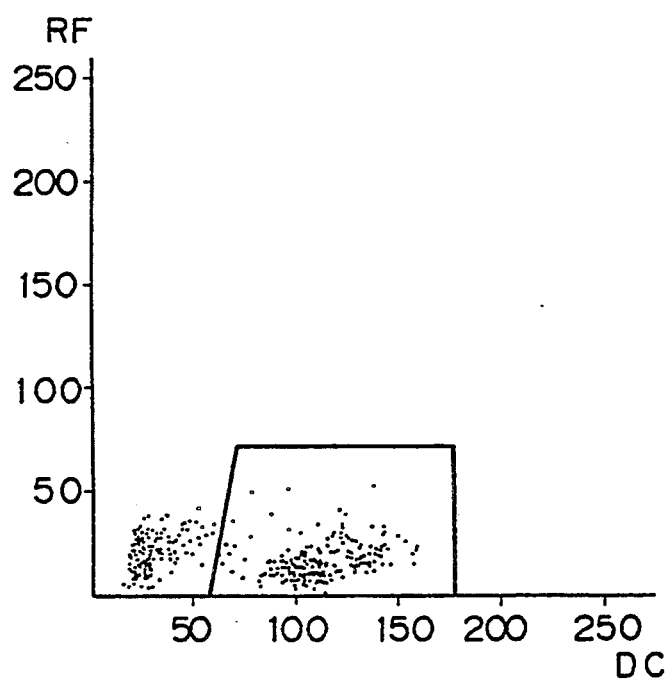
FIG. 5 is a two-dimensional distribution diagram showing the results of leukocyte classification conducted in Example 4 by the combination of the RF and DC methods using a reagent for the measurement of basophils.
Figure 6:
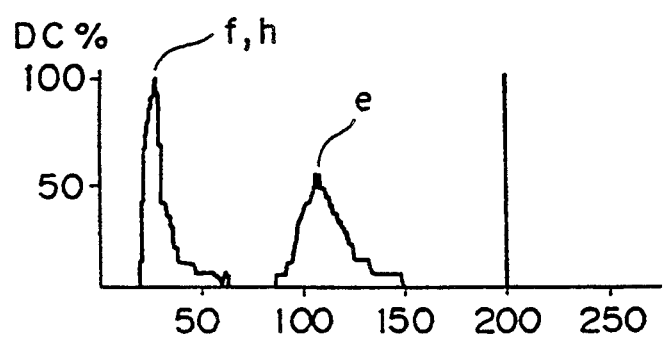
FIG. 6 is a graph showing the results of leukocyte classification conducted by the DC method as done in Example 4.

The results of measurement conducted by the combination of the RF and DC methods are shown in FIG. 5, and the results of measurement conducted by the DC method alone are shown in FIG. 6. In either case, basophils were selectively left intact and could be measured as separate entities from the other leukocytes. This is because the lysing agent used caused the nuclei of all leukocytes other than basophils to become naked, leaving only basophils intact.

Surfactants that can be used in the reagent for basophil measurement described above are not limited to Emulgen 123-P and may be selected from among any nonionic surfactants that are represented by the general formula: R-O-$(CH_2CH_2O)_nH$, provided that R is an alkyl group having 10–20 (preferably 12–18) carbon atoms, and n is 6–100 (preferably 15–40). Hydrochloric acid and nitric acid are used to adjust the pH to about 3.0 and at least one acid may be selected from the group consisting of hydrochloric acid, nitric acid and acetic acid. The osmotic pressure may be of any value within the range of 10–400 (preferably 20–100). The solution temperature may be any value within the range of 10°–40° C.

While the basophils are classified and counted as described above, lymphocytes, monocytes, granulocytes and eosinophils in the granulocytes are classified and counted by the method employed in Example 3. The number of neutrophils is calculated by subtracting the numbers of eosinophils and basophils from the total granulocyte count. In this way, the numbers and percentages of lymphocytes, monocytes, neutrophils, eosinophils and basophils in all the leukocytes of interest can be determined.

Similar measurements were conducted on 105 specimens of blood by the methods described above and the results were compared with the performance of the visual counting method by which 500 cells were observed per specimen. The correlation coefficients for the percentages of five leukocyte types are shown in Table 2.

TABLE 2

| | |
|---|---|
| Lymphocytes | 0.95 |
| Monocytes | 0.43 |
| Neutrophils | 0.90 |
| Eosinophils | 0.95 |
| Basophils | 0.85 |

As the above data shows, the method employed in Example 4 showed good correlation with the visual counting method which is the standard technique currently employed for classifying and counting leukocytes, and it will be understood that the method of the present invention is capable of clearly classifying the leukocytes into five types and counting their respective numbers. The results obtained in Example 4 are dramatic in that they show the first success in classifying and differentiating the leukocytes into five types by a method which depends on electrical detection of the change in impedance that occurs when corpuscles pass through an orifice.

EXAMPLE 5

A composition of the two-component regent system of the first embodiment of the present invention and the results of a measurement conducted using said reagent are described below.

| Composition of reagent | |
|---|---|
| First fluid (liquid diluent) | |
| Buffer agents: | |
| Disodium phosphate (dodecahydrate) $Na_2HPO_4.12H_2O$ | 9.0 g |
| Monosodium phosphate (anhydrous) $NaH_2PO_4$ | 3.0 g |
| Antioxidant: | |
| EDTA-2K | 0.1 g |
| Electroconductivity adjusting agent: | |
| Sodium chloride (NaCl) | 0.16 g |
| Solubilizing agent: | |
| CHAPS | 0.4 g |
| Hyperosmotic agent: | |
| Ethylene glycol | 70.0 g |
| Fixing agent: | |
| Formalin | 50.0 g |
| Water (pH 7.2; osmotic pressure, 1400 mOsm) | 1000 ml |
| Second fluid (lysing reagent) | |
| Buffer agents: | |
| Disodium phosphate (dodecahydrate) $Na_2HPO_4.12H_2O$ | 9.0 g |
| Monosodium phosphate (anhydrous) $NaH_2PO_4$ | 3.0 g |
| Antioxidant: | |
| EDTA-2K | 0.1 g |
| dl-methionine | 1.0 g |
| Fixing agent: | |
| Formalin | 30.0 g |
| Polyoxyethylene-based surfactant: | |
| E-212 [$C_{18}H_{35}$—O—$(CH_2CH_2O)_{12}$—H] | 0.5 g |
| Water (pH 7.2; osmotic pressure, 920 mOsm) | 1000 ml |

Figure 7:
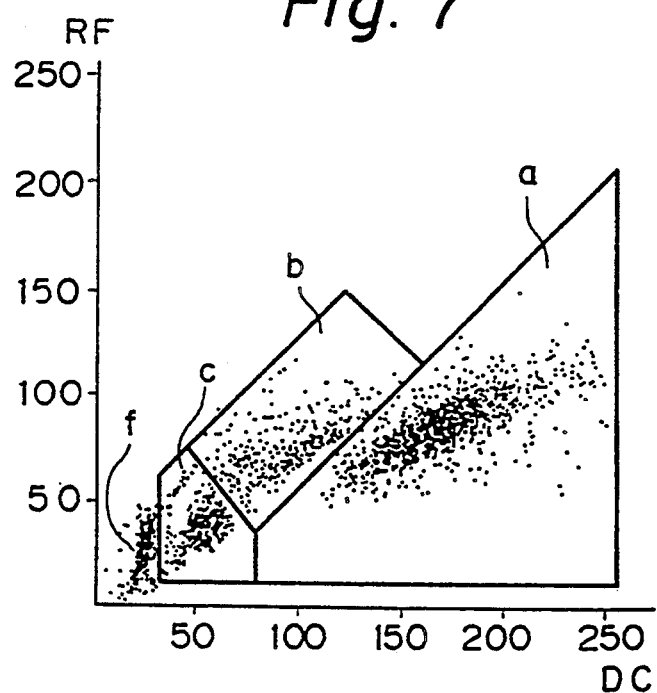
FIG. 7 is a two-dimensional distribution diagram showing the results of leukocyte classification conducted in Example 5.

Blood (12 μl) that had been left to stand for 4 hours after sampling was mixed with 2 ml of the first fluid having a solution temperature of 26° C., and the mixture was left to stand for 25 seconds. Thereafter, 1 ml of the second fluid having a solution temperature of 26° C. was added to make a 250-fold diluted sample. A measurement was conducted for 6 seconds following the lapse of 60 seconds after the addition of the second fluid. The results are shown in FIG. 7. The leukocytes were classified into three types, granulocytes a, monocytes h and lymphocytes c.

EXAMPLE 6

Another composition of the two-component reagent system of the first embodiment of the present invention and the results of a measurement conducted using said reagent are described below.

| Composition of reagent | |
|---|---|
| First fluid (liquid diluent) | |
| Buffer agents: | |
| Disodium phosphate (dodecahydrate) $Na_2HPO_4.12H_2O$ | 18.0 g |
| Monosodium phosphate (anhydrous) $NaH_2PO_4$ | 2.3 g |
| Antioxidant: | |
| EDTA-2K | 0.1 g |
| dl-methionine | 1.0 g |
| Electroconductivity adjusting agent: | |
| Sodium chloride (NaCl) | 2.5 g |
| Solubilizing agent: | |
| CHAPS | 0.4 g |
| Hyperosmotic agent: | |
| Ethylene glycol | 70.0 g |
| Ethanol | 100.0 g |
| Fixing agent: | |
| Formalin | 100.0 g |
| Polyoxyethylene-based surfactant: | |

-continued

| Composition of reagent | |
|---|---|
| E-212 [$C_{18}H_{35}$—O—$(CH_2CH_2O)_{12}$—H] | 0.06 g |
| Water (pH 7.4; osmotic pressure, 3000 mOsm) | 1000 ml |
| Second fluid (lysing reagent) | |
| Buffer agents: | |
| Disodium phosphate (dodecahydrate) $Na_2HPO_4.12H_2O$ | 14.0 g |
| Monosodium phosphate (anhydrous) $NaH_2PO_4$ | 1.5 g |
| Antioxidant: | |
| EDTA-2KI | 0.1 g |
| dl-methionine | 1.0 g |
| Electroconductivity adjusting agent: | |
| Sodium chloride (NaCl) | 2.3 g |
| Fixing agent: | |
| Formalin | 100.0 g |
| Polyoxyethylene-based surfactant: | |
| E-212 [$C_{18}H_{35}$—O—$(CH_2CH_2O)_{12}$—H] | 0.06 g |
| Water (pH, 7.2; osmotic pressure, 1380 mOsm) | 1000 ml |

Figure 8:
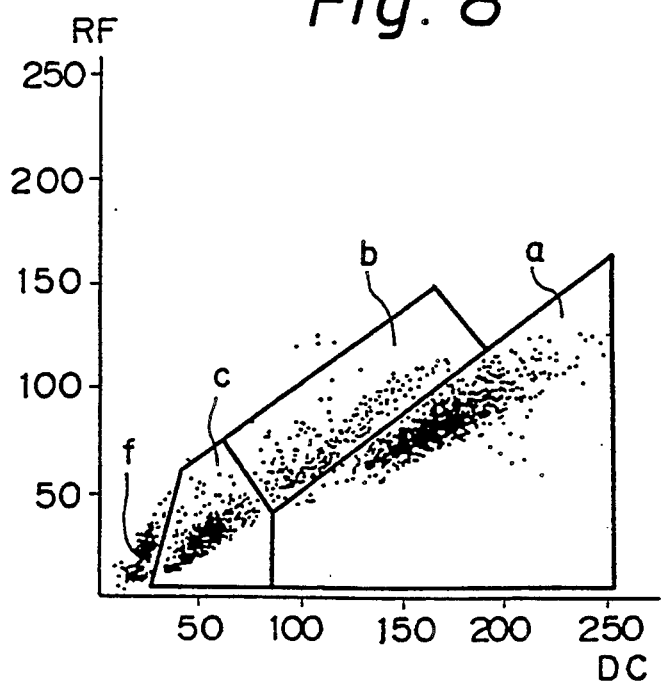
FIG. 8 is a two-dimensional distribution diagram showing the results of leukocyte classification conducted in Example 6.
Figure 9:
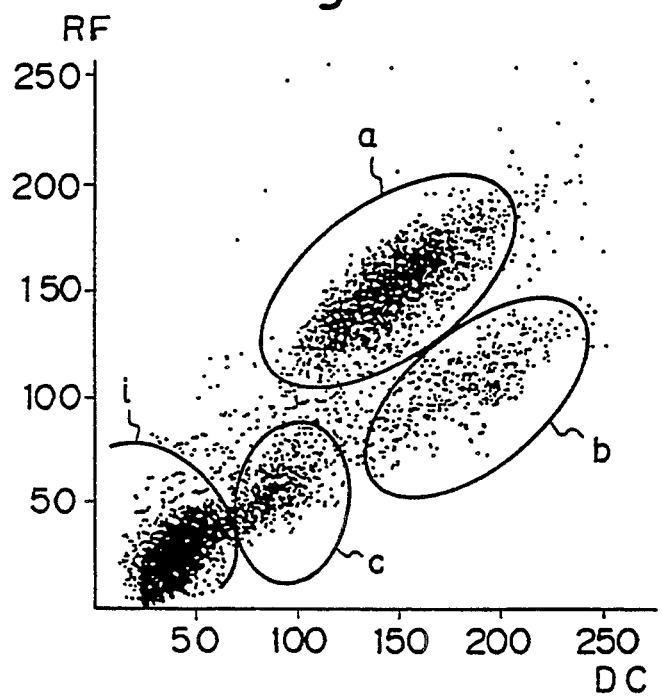
FIG. 9 is a two-dimensional distribution diagram obtained when a blood sample diluted in the absence of a cytolytic agent was measured by the RF and DC methods.
Figure 10:
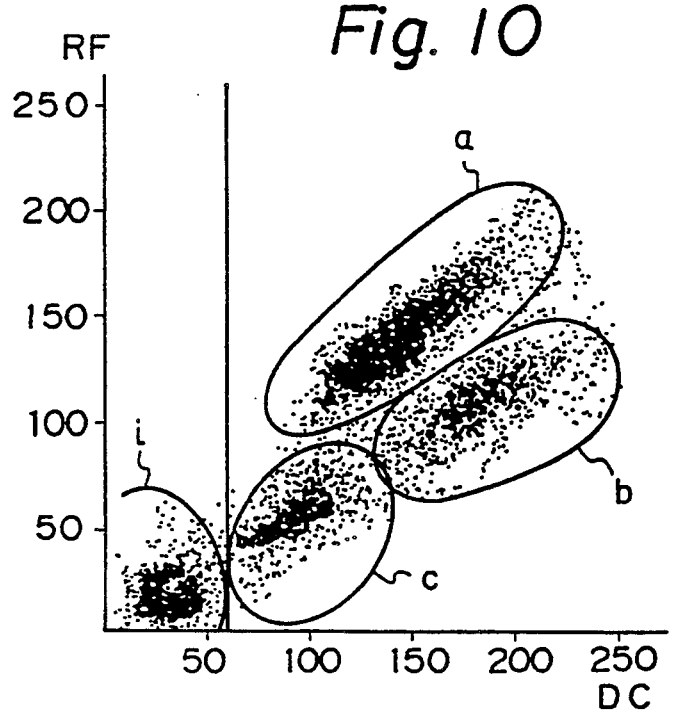
FIG. 10 is a two-dimensional distribution diagram obtained when blood in which only leukocytes were separated in the absence of a cytolytic agent was measured by the RF and DC methods.
Figure 11:
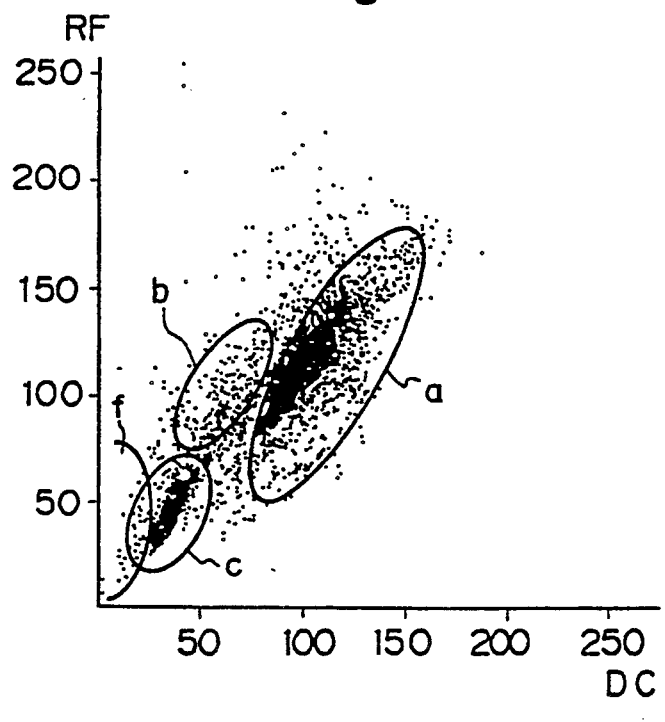
FIG. 11 is a two-dimensional distribution diagram obtained when a blood sample containing the same cytolytic agent as that used in Example 2 was measured by the RF and DC methods; the scale of FIG. 11 is the same as that of FIGS. 9 and 10; and the scale of FIG. 2 is enlarged as compared to FIG. 11.
Figure 12:
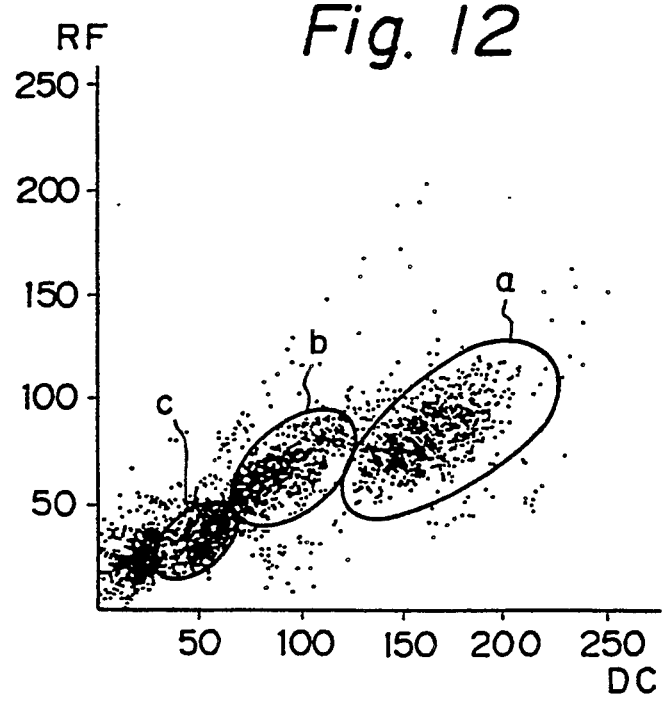
FIG. 12 is a two-dimensional distribution diagram obtained when a blood sample that had been left to stand for 8 hours after sampling and to which a reagent containing no hyperosmotic agent was added was measured by the RF and DC methods.
Figure 13:
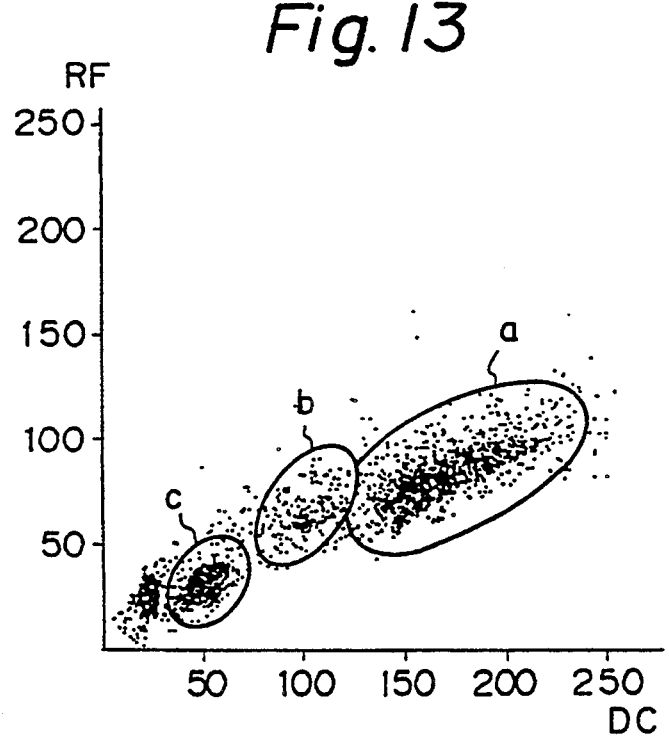
FIG. 13 is a two-dimensional distribution diagram obtained when a blood sample that had been left to stand for 8 hours after sampling and to which a reagent containing a hyperosmotic agent was added was measured by the RF and DC methods.
Figure 14:
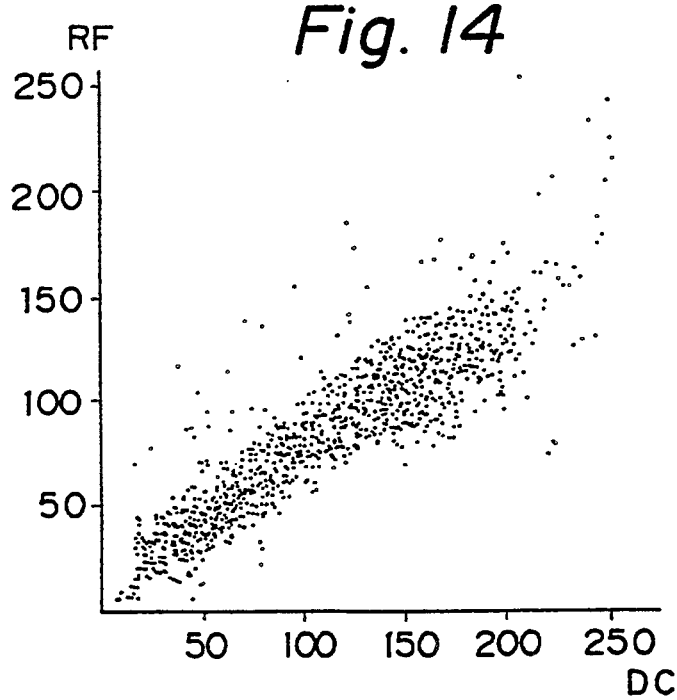
FIG. 14 is a two-dimensional distribution diagram showing the results of leukocyte classification conducted by the RF and DC methods using a quaternary ammonium salt as a cytolytic agent.
Figure 15:
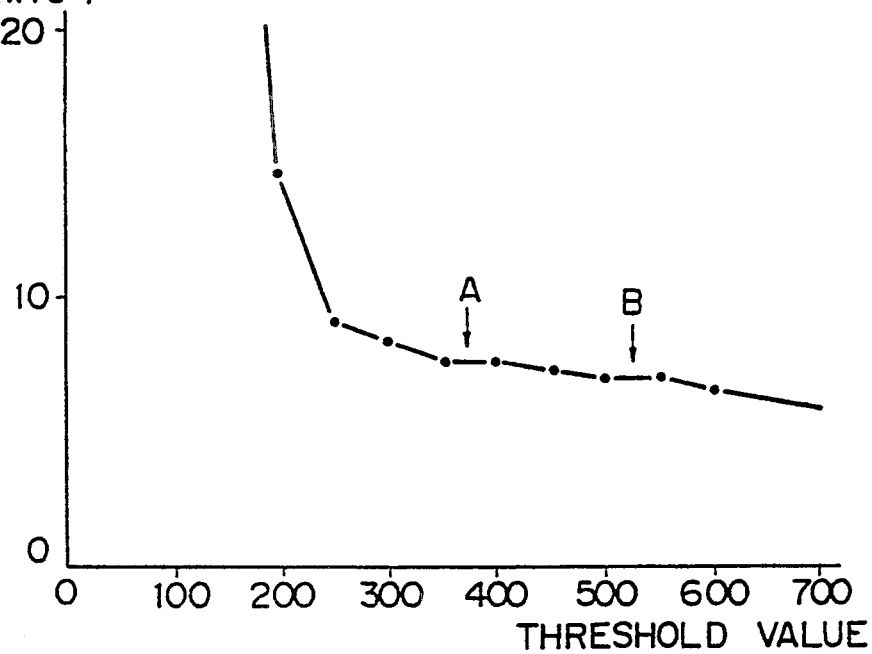
FIG. 15 is a cumulative size-frequency distribution curve enabling one to confirm that the magnitude of signals from leukocytes is sufficiently large as compared to the magnitude of signals from erythrocyte membranes (ghosts) and noise; the horizontal axis of the graph in the diagram plots the signal threshold values of an automatic blood cell counter, and the vertical axis plots the number of detected signals exceeding a certain signal threshold value.
Figure 16:
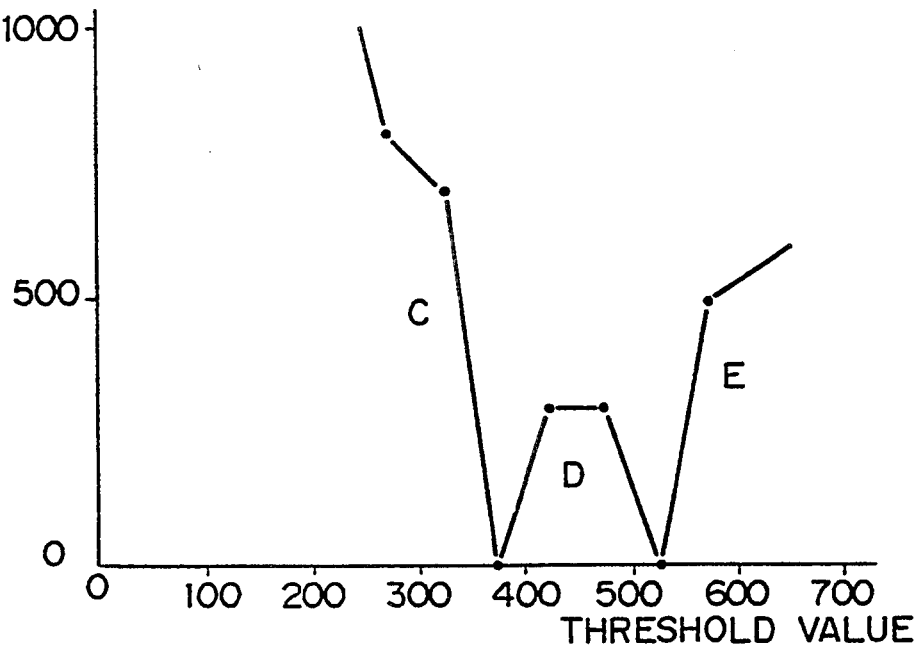
FIG. 16 is a size-frequency distribution curve constructed by plotting the number of leukocytes for each threshold level as calculated from the cumulative size-frequency distribution curve in FIG. 15; in this diagram, C signifies the population of erythrocyte ghosts and noise, D is the first population of leukocytes, and E is the second population of leukocytes.

Blood (12 μl) that had been left to stand for 4 hours after sampling was mixed with 2 ml of the first fluid having a solution temperature of 26° C., and the mixture was left to stand for 20 seconds. Thereafter, 1 ml of the second fluid having a solution temperature of 26° C. was added to make a 250-fold diluted sample. A measurement was conducted for 6 seconds following the lapse of 40 seconds after the addition of the second fluid. The results are shown in FIG. 8. The leukocytes were classified into three types, granulocytes a, monocytes b and lymphocytes c.

While the leukocytes were classified into three types by the method described in Example 6, the eosinophil and basophil counts were obtained by the methods described in Examples 3 and 4, respectively. The overall results were compared with those obtained for 50 specimens of blood by the visual counting method as in Example 2. The correlation coefficients determined from this comparison are shown in Table 3.

TABLE 3

| Lymphocytes | 0.98 |
|---|---|
| Monocytes | 0.83 |
| Neutrophils | 0.95 |
| Eosinophils | 0.95 |
| Basophils | 0.81 |

The data in Table 3, as compared to that in Table 3, shows a significant improvement in the correlation coefficient for monocytes.

In Examples 5 and 6, the pH was adjusted to 7.2 and 7.4, respectively, but it should be understood that pH's in the range of 6-8 will suffice.

EXAMPLE 7

The results of detections of abnormal leukocyte cells using the reagent described in Example 2 are shown below.

FIG. 19 shows the results of a measurement of blood from a patient with acute lymphocytic leukemia (ALL). Obviously, lymphoblasts n appeared. Detecting the appearance of lymphoblasts allows one to discover the existence of lymphocytic leukemia.

FIG. 20 shows the results of a measurement of blood from a patient with adult T-cell leukemia (ATL). Obviously, heterolymphocytes m appeared. Detection of the appearance of heterolymphocytes might well lead one to suspect the existence of a lymphocytic disease.

Figure 21:
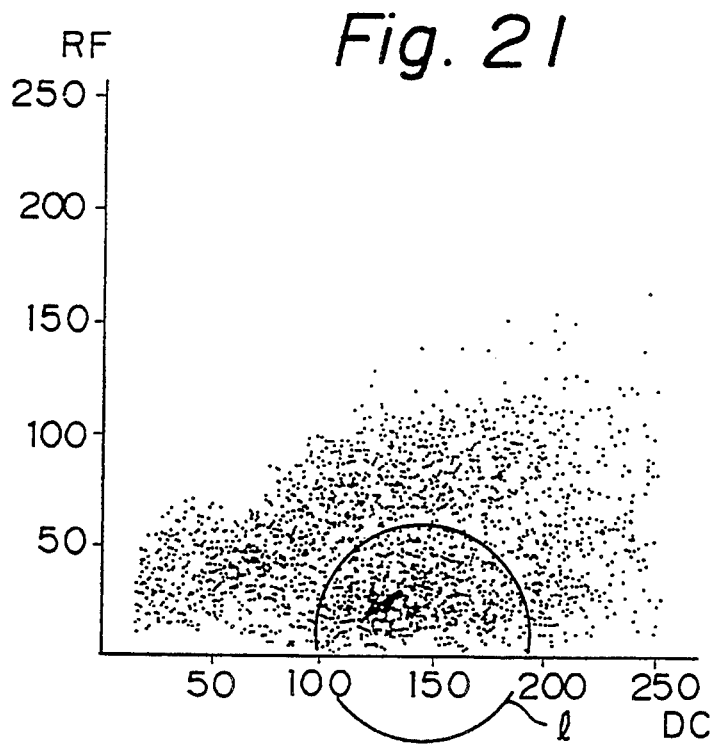
FIGS. 21 and 22 are two-dimensional distribution diagrams as obtained in the measurement of blood from a patient with acute myelocytic leukemia (AML).

FIG. 21 shows the results of a measurement of blood from a patient with acute myelocytic leukemia (AML). Obviously, blasts l appeared. Detecting the appearance of blasts allows one to discover the existence of myelocytic leukemia.

Figure 22:
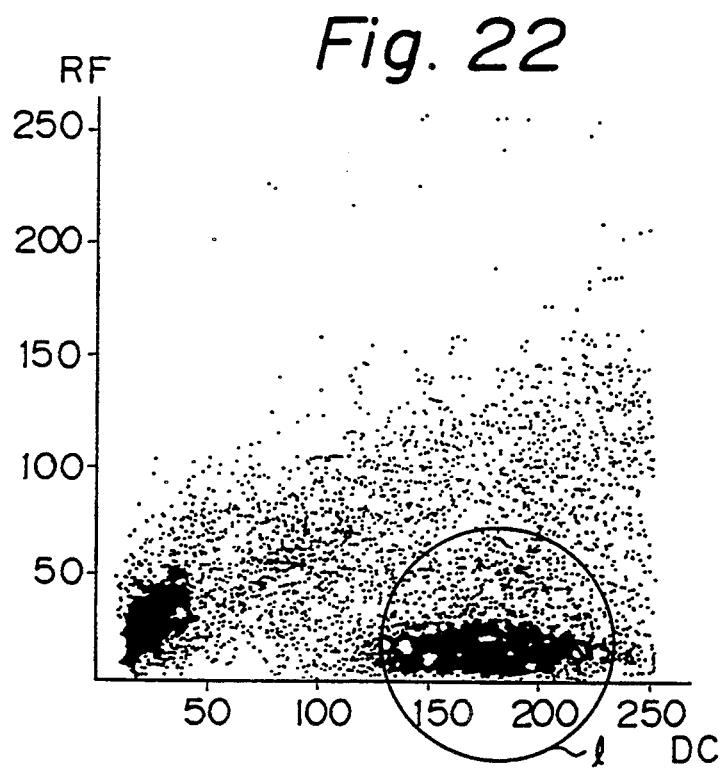

FIG. 22 also shows the results of a measurement of blood from a patient with acute myelocytic leukemia (AML). The appearance of blasts l is marked.

Figure 23:
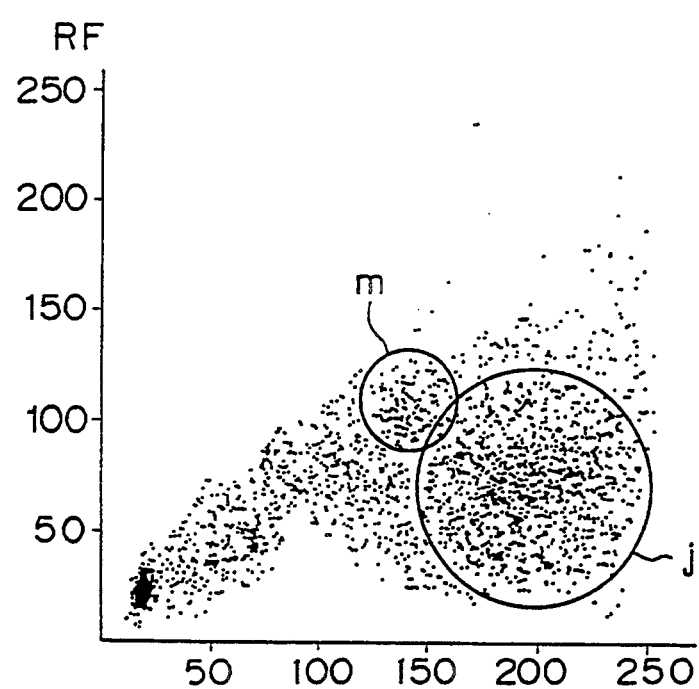
FIG. 23 is a two-dimensional distribution diagram for the case where left shifts j and heterolymphocytes m appeared in one specimen.

FIG. 23 shows a case where left shifts j and heterolymphocytes m appeared in one specimen.

Figure 24:
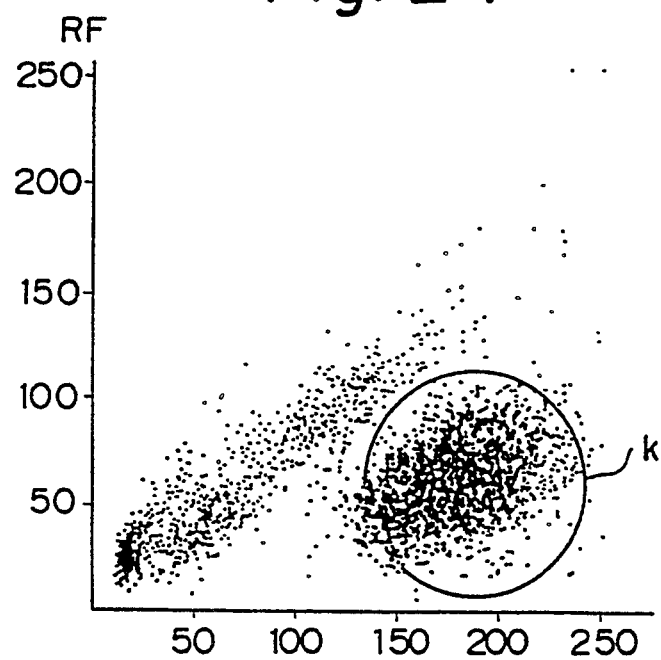
FIGS. 24 and 25 are two-dimensional distribution diagrams for the case where immature granulocytes k appeared.

FIG. 24 shows a case of the appearance of immature granulocytes k.

Figure 25:
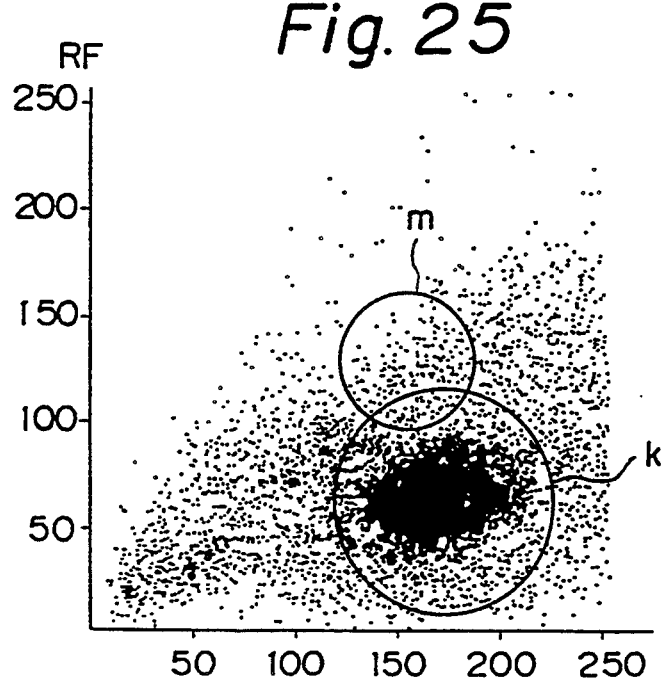

FIG. 25 shows a typical case of the appearance of immature granulocytes k and heterolymphocytes m.

Various layouts can be adopted for implementing the methods of the first embodiment of the present invention in practical applications using specific analyzers.

The simplest way that can be conceived of is as follows: three detecting portions are provided, the first one having a channel for measurement by the RF method (to be hereinafter referred to as a RF channel) and a channel for measurement by the DC method (to be hereinafter referred to as a DC channel), the second one having only a DC channel, and the third one also having only a DC channel; in the first detecting portion, the leukocytes are classified into lymphocytes, monocytes and granulocytes and their respective numbers are counted using a reagent for leukocyte classification; in the second detecting portion, the number of basophils is counted using a reagent for basophil measurement; and in the third detecting portion, only eosinophils are left intact using a reagent for leukocyte classification and the number of the eosinophils is counted so as to determine the neutrophil count be calculation. However, in this method, a different sample for measurement must be prepared for each of the three detecting portions and a need therefore arises for providing different cytolytic agents or liquid diluents, as well as storage tanks and other necessary accessories; this inevitably leads to the use of a complicated and bulky apparatus.

This defect could be eliminated by using the lysing agent described in Example 2. A method adopting this approach will proceed as follows: two detecting portions are provided, the first one having RF and DC channels, and the second one having only a DC channel; in the first detecting portion, the leukocytes are classified into lymphocytes, monocytes and granulocytes and their respective numbers are counted in the manner described above; after the lapse of a predetermined period of time when only eosinophils are selectively left intact, their number is counted; in the second detecting portion, only the number of basophils is counted in the manner described above. This method offers the advantage that the overall composition of the equipment is much simplified since only two kinds of cytolytic agent need be employed and there is no need to provide more than two detecting portions. However, with this method, the operator has to wait for a certain period of time until the eosinophils reach the state where they can be counted, so the method is not preferred for use with an automatic analyzer which is required to perform continuous measurement of many specimens in a short period of time.

This problem could be solved by providing the third detecting portion having a DC channel as in the first method. After classifying the leukocytes into three types in the first detecting portion, the spent lysing fluid is transferred to the third detecting portion, where the number of eosinophils is counted after the lapse of a predetermined standby period. In the meantime, a lysing fluid for measuring the next specimen is prepared in the first detecting portion and the measurement for classification into three types is conducted simultaneously with the counting operation in the third detecting portion. In this way, a number of specimens can be measured on a continuous basis without any interruption.

In a case where reduction in the processing time per specimen is not an important factor, the third detecting portion for measuring eosinophils may be dispensed with and the following scheme may be adopted: after the counting of the number of basophils is completed in the second detecting portion, the sample solution is withdrawn and the lysing fluid on which the measurement for classification into three types has been completed in the first detecting portion is transferred to the second detecting portion having a DC channel, in which eosinophil counts are obtained after the lapse of a certain standby period.

If abnormal leukocyte cells appear, they are detected in the detecting portion for classification into three types in any of the apparatus layouts described above.

The second embodiment of this invention is illustrated in the following examples but it is not limited to or by these specific examples.

REFERENCE EXAMPLE

Figure 31:
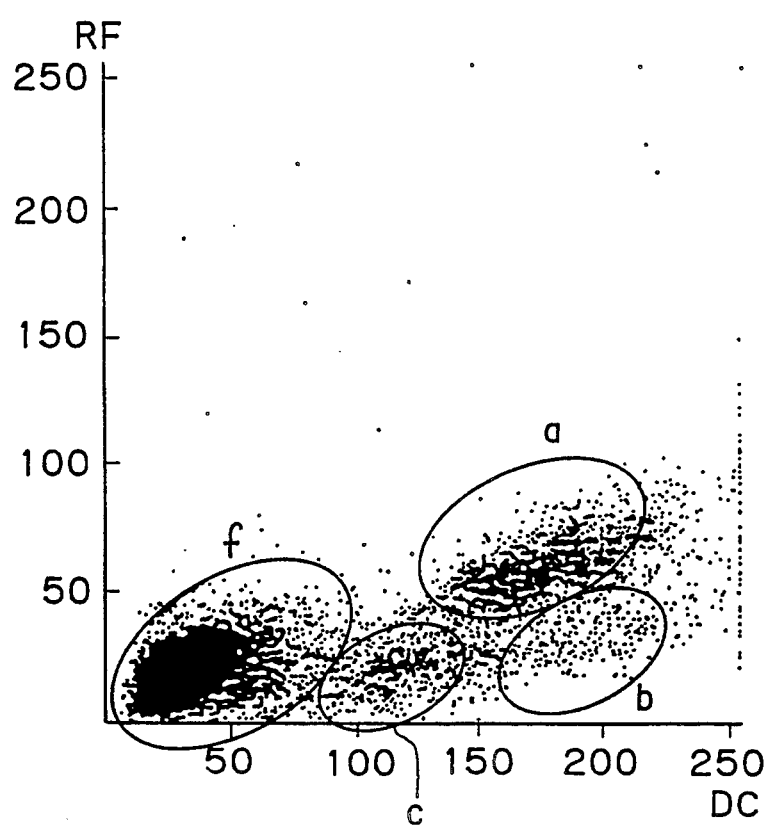
FIG. 31 and 32 are scattergrams showing the distributions of results obtained by measuring blood merely hemolyzed in an acidic and hypoosmotic solution immediately after blood gathering and 24 hours after blood gathering respectively.

Erythrocytes in a blood sample were hemolyzed and leukocytes in the sample were determined by using a reagent solution wherein the pH was kept at 2.0 and the osmolarity was adjusted to 80 mOsm/kg. The results are indicated in FIG. 31. The horizontal and vertical axes of each of the figures represent signal strengths as determined by the DC and the RF methods respectively. Each spot given in FIG. 31 corresponds to a cell which showed the corresponding DC signal strength and RF signal strength.

FIG. 31 shows the results obtained from blood immediately after gathering. In this figure, distribution of erythrocyte ghosts f and that of lymphocytes c are overlapped in part and distribution of granulocytes a, monocytes b and lymphocytes c are poorly separated.

Figure 32:
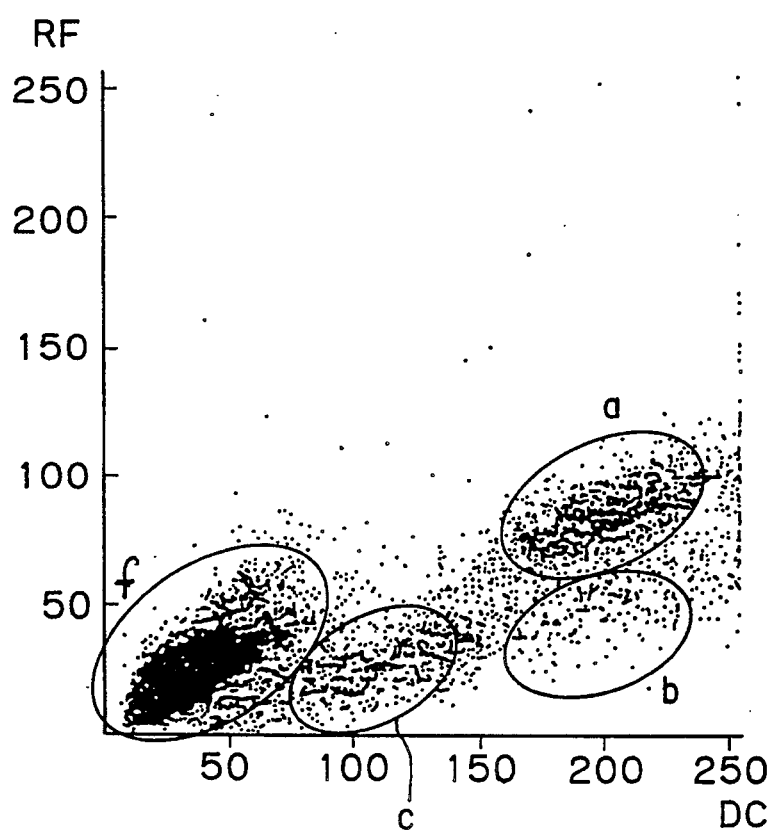

FIG. 32 indicates the results obtained by determination of blood 24 hours after gathering but by using the same reagent as FIG. 31. Distributions of the three kinds of leukocytes are more poorly separated from each other.

EXAMPLE 8

Figure 26:
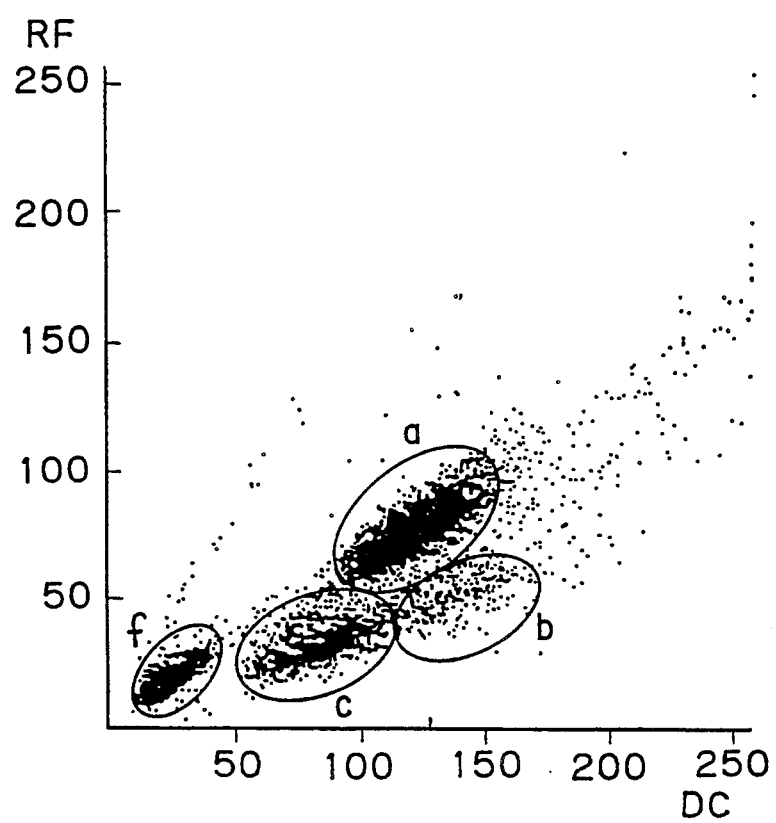
FIG. 26 is a scattergram showing the distribution of results obtained by measuring leukocytes in a freshly taken blood sample using a single solution reagent in accordance with the second embodiment of the invention.

The results obtained when determining blood immediately after gathering by using a reagent in accordance with the second embodiment of the invention are indicated in FIG. 26. The pH of the solution was 2.0 and the osmolarity thereof was 80 mOsm/kg. A polyoxyethylene based nonionic surfactant of Emulsit 9

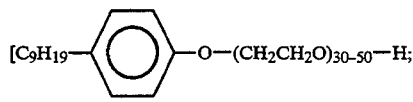

$[C_9H_{19}$—⟨○⟩—$O$—$(CH_2CH_2O)_{30-50}$—$H$;

manufactured by Daiichi Kogyo Seiyaku Kabushiki Kaisha] was used at a concentration of 1.5 g/l. Distribution of erythrocyte ghosts f and that of lymphocytes c are clearly separated without overlapping and distribution of granulocytes a and monocytes c are well separated.

EXAMPLE 9

Figure 27:
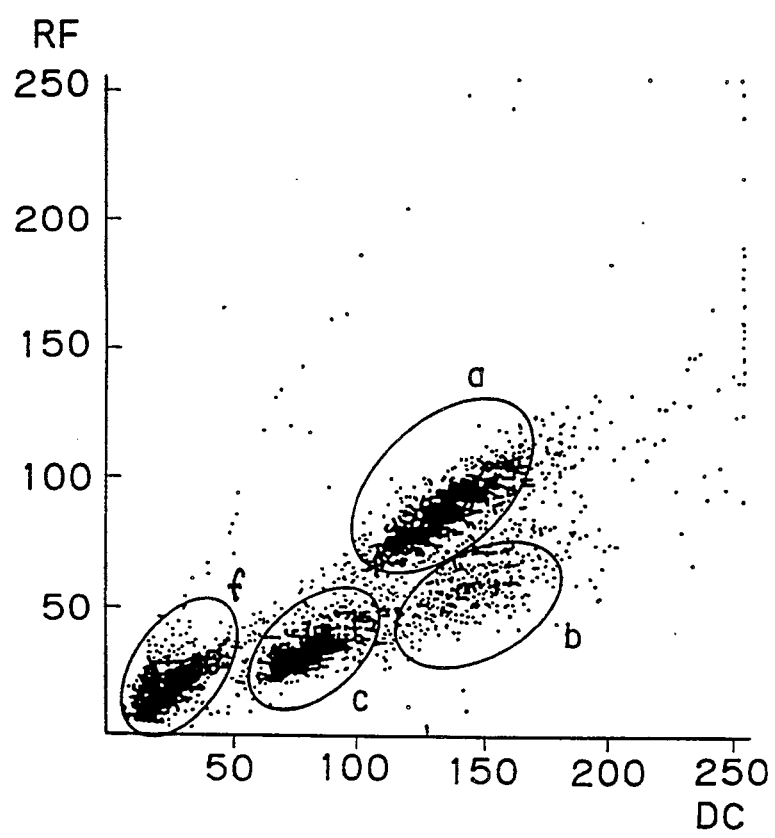
FIG. 27 is a scattergram showing the distribution of results obtained by measuring leukocytes 24 hours after a blood sample is taken using a single solution reagent in accordance with the second embodiment of the invention.

FIG. 27 indicates the results obtained when determining blood 24 hours after gathering by using the same reagent as FIG. 26. As shown in FIG. 27, distributions of the three kinds of leukocytes and distribution of erythrocyte ghosts are well separated. Thus, use of the reagent above can minimize the effect of erythrocyte ghosts and can accomplish a stable counting and classification of leukocytes in a blood sample gathered a long time ago.

Figure 33:
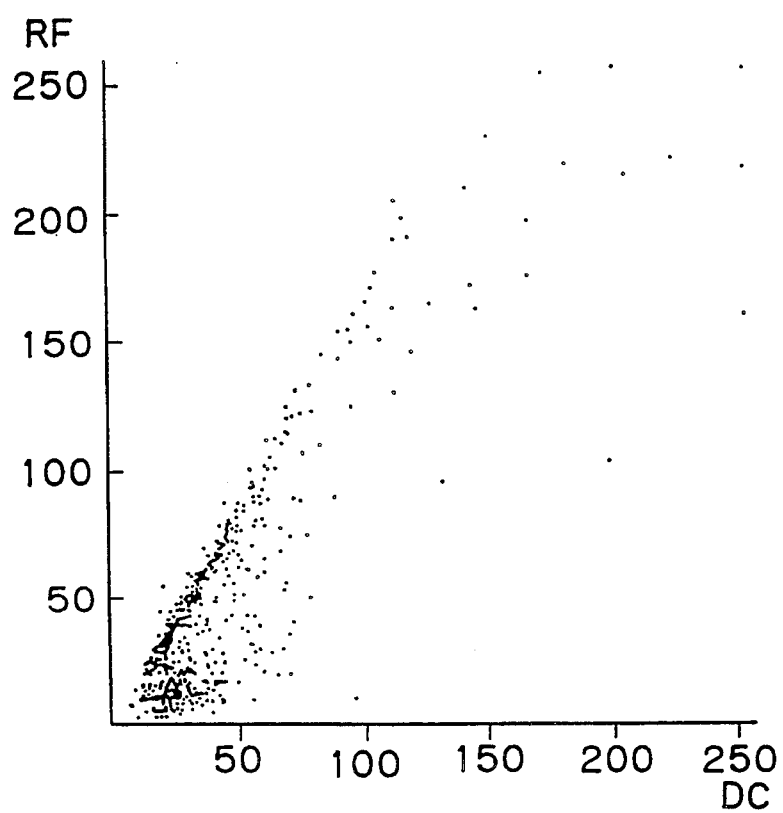
FIG. 33 is a scattergram showing the distribution of results obtained by measuring leukocytes in a freshly taken blood sample using a polyethylene based nonionic surfactant having only ten recurring oxyethylene units.

FIG. 33 indicates the results obtained by determining the same blood as FIG. 26 by using as a polyoxyethylene based nonionic surfactant Actinol L10 $[C_{12}H_{25}$—$O$—$(CH_2CH_2O)_{10}$-$H$; manufactured by Matsumoto Yushi Seiyaku Kabushiki Kaisha] in place of Emulsit 9. According to FIG. 33, classification and counting of leukocytes became impossible because not only erythrocytes but also leukocytes were destroyed or remarkably contracted. The smaller the number of recurring oxyethylene units, the stronger is the hemolytic activity thereof. Actinol L10 wherein n is 10 destroyed or contracted not only erythrocytes but also leukocytes.

On the contrary, the larger the number of recurring oxyethylene units, the weaker its hemolytic activity becomes. For a surfactant wherein n is large, weak hemolytic activity causes damage to leukocytes to be remarkably reduced. Therefore, use of such a surfactant makes possible classification and counting of leukocytes even in blood which was gathered a long time ago. On the other hand, if hemolytic activity of the surfactant is too weak, erythrocyte ghosts cannot be sufficiently reduced and cannot be well distinguished from lymphocytes.

However, surprisingly the inventors found that the erythrocyte ghosts can be sufficiently reduced without causing undesirable leukocytes damage by using the nonionic surfactant wherein the addition mole number of polyoxyethylene is 20–100.

Moreover, the inventors also found that the surfactant protects leukocyte membranes and can provide definite separation into three groups of leukocytes: granulocytes a; monocytes b; and lymphocytes c on a two dimensional distribution chart.

An example of said protecting effects is given below:

When hemolyzation was conducted in an acidic and hypoosmotic solution, leukocytes were damaged and contracted in about 5 minutes. But when a nonionic surfactant wherein the addition mole number of polyoxyethylene is 20–100 is added to the solution, leukocytes do not contract even after 20 minutes has passed.

As indicated above, the reagent can be practiced in the form of one solution. One-solution type reagent is better than the conventional two-solution type regent in an automatic blood analyzer because the construction of the apparatus can be simplified and the cost thereof can be reduced.

This invention, however, is not limited only to a single solution type reagent. Reagents of the two-solution type are described as follows:

The first of the two solutions provided in the two-solution type reagent is identical to the reagent described above and is reacted with blood to make erythrocytes hemolyze under an acidic and hypoosmotic condition with injury to leukocytes being minimized.

The second of the two solutions is added to the reaction solution containing the first solution and the blood, whereby pH and osmolarity of the resulting mixture are adjusted to neutral (pH 5.0-12.0) and equivalent to high osmolarity (150-2000 mOsm/kg). Thus, the second of the two solutions has effects of adjustment of pH and osmolarity of the reaction solution. By adding the second solution, separation of groups of lymphocytes, monocytes and granulocytes is improved, whereby analysis of a two-dimensional distribution by a computer to fractionate the distribution into each group is made easy.

Incidentally, separation of said groups can be further improved by incorporating an additional amount of polyoxyethylene based nonionic surfactant and a solubilizing agent.

EXAMPLE 10

Reaction of the two-solution is illustratively described below.

Preparation of the first solution

To 1 l of a solution kept at pH 2.0 and adjusted to 80 mOsm/kg with a potassium chloride, hydrochloric acid buffer 1.5 g of Emulsit 9 was added.

Preparation of the second solution 2 l of a monosodium phosphate/disodium phosphate buffer was added to 100 g of formalin. After the resulting solution was adjusted to pH 7.5 and 1100 mOsm/kg, 2.5 g of B-phenethyl alcohol was added as a preservative, 10 g of triethanolamine as an antioxidant and 0.025 g of Emulgen 420 [$CH_3(CH_2)_7CH=CH(CH_2)_8-O-(CH_2CH_2O)_{13}H$; a polyoxyethylene based nonionic surfactant manufactured by Kao Kabushiki Kaisha] as an agent for constructing erythrocyte ghosts were added to said solution.

Reaction Condition

To 5 ml of the first solution 60 μl of blood was added and the mixture was reacted at 33° C. for 30 seconds. Thereafter, the second solution was added to the mixture and the resulting mixture was reacted at 33° C. for 30 seconds.

Figure 28:
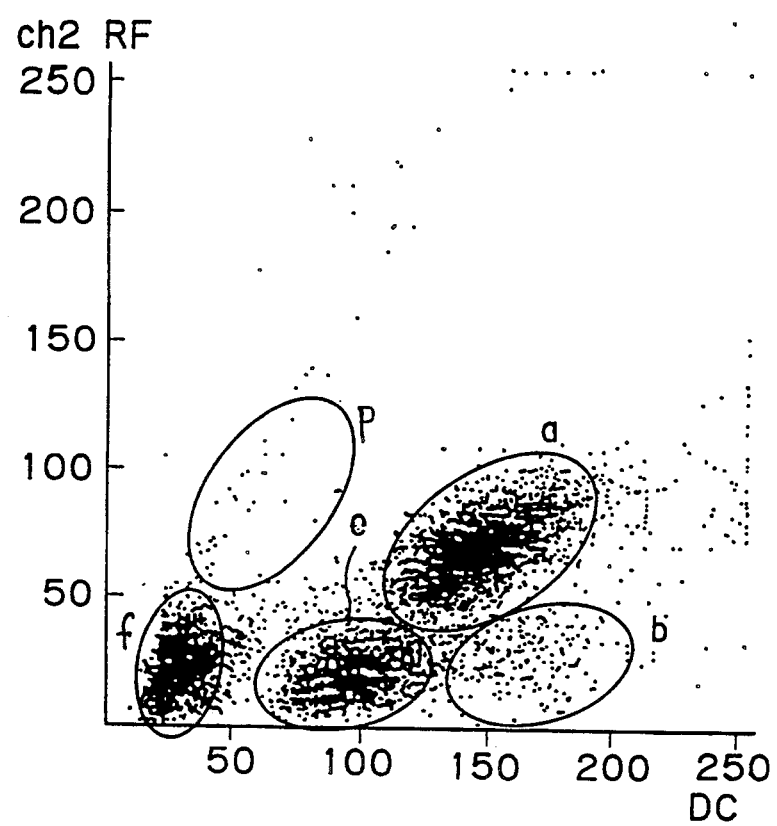
FIG. 28 is a scattergram showing the distribution of results obtained by measuring leukocytes in a freshly taken blood sample using a two solution reagent in accordance with the second embodiment of the invention.

The two dimensional distribution obtained by subjecting blood to the above two step reaction immediately after blood gathering are indicated in FIG. 28. As shown in FIG. 28, erythrocyte ghosts f were sufficiently contracted and granulocytes a, monocytes b and lymphocytes c were well separated. The symbol p represents a platelet aggregation.

Figure 29:
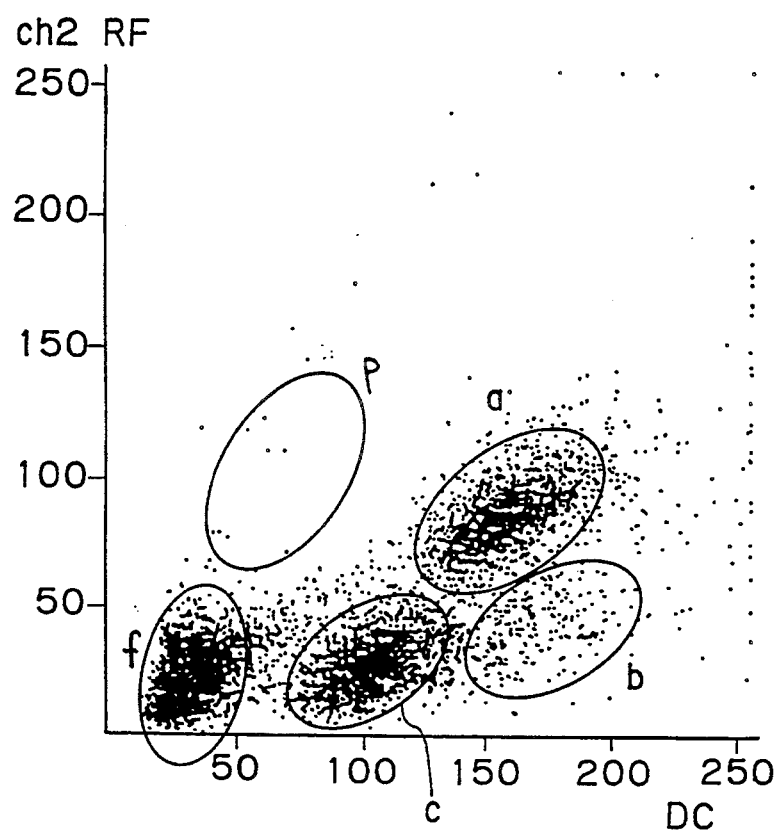
FIG. 29 is a scattergram showing the distribution of results obtained by measuring leukocytes 24 hours after a blood sample is taken using a two solution reagent in accordance with the second embodiment of the invention.

FIG. 29 indicates the results obtained by determining in the same manner as in FIG. 28 the same blood as in FIG. 28 except that 24 hours passed after blood gathering. As clearly shown in FIG. 29, even if determination was carried out 24 hours after blood gathering, substantially the same two dimensional distribution as in FIG. 28 was obtained. This proves that the reagent of the second embodiment of this invention could realize a stable determination of blood a long time after gathering. This result depends on stabilization of leukocytes with the reagent of the second embodiment of this invention.

Leukocytes were classified into three fractions and, as described above in the first embodiment of the present invention, a sample for determination of eosinophils and a sample for determination of basophils were prepared to measure the number of eosinophils and basophils. By the procedures, the leukocytes could be classified into five types, that is, lymphocytes, monocytes, neutrophils, eosinophils and basophils and cells of each type could be counted to obtain the total number of cells of each type of leukocytes and ratios thereof. Coefficients of correlation for ratios of five types of leukocytes obtained by comparing the results from determination of 20 blood samples according to the above method with those obtained by measuring 200 cells per each of said samples by the visual counting method are indicated in Table 1.

TABLE 1

| | |
|---|---|
| lymphocytes | 0.987 |
| monocytes | 0.900 |
| neutrophils | 0.985 |
| eosinophils | 0.979 |
| basophils | 0.525 |

Figure 30:
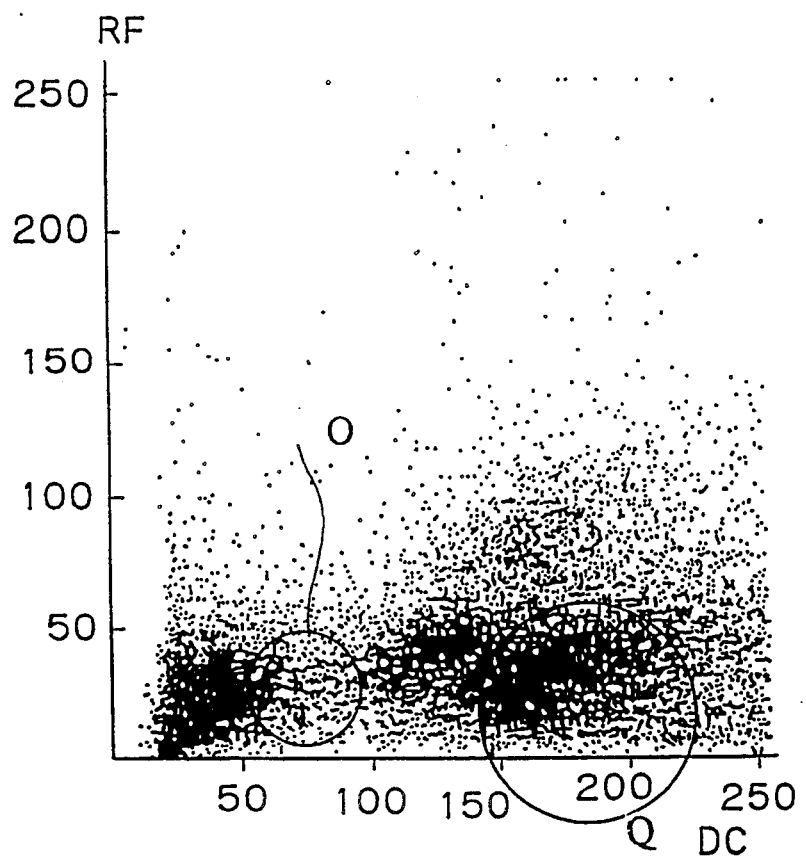
FIG. 30 is a scattergram indicating the distribution of results obtained by measuring blood of a subject suffering from acute myelocytic leukemia using a two solution reagent in accordance with the second embodiment of the invention.

In the same manner, blood of a patient with acute myelocytic leukemia (AML) was determined and the results are indicated as a two-dimensional distribution given in FIG. 30.

Symbols q and o mean leukemia cells and nucleate erythrocytes respectively. In FIG. 30, abnormal cells such as leukemia cells appear at the locations at which no cell is present in FIGS. 28 and 29. Thus, according to this invention, not only normal cells but also abnormal cells can be detected. In accordance with the reagent and process of the second embodiment of this invention, erythrocytes can be hemolyzed by using a cytolytic agent having a stable hemolytic activity; leukocytes can be rapidly stabilized; and erythrocyte ghosts and lymphocytes can be distinguished clearly; and combination of the DC method and the RF method can realize classification of leukocytes blood into five types of normal leukocytes and abnormal cells; and accurate classification values can be obtained even for blood tested a long time after being gathered.

What is claimed is:

1. A reagent for classifying leukocytes in a blood sample that lyses erythrocytes and which acts on leukocytes to enable the classification and counting of leukocytes, said reagent comprising (a) a first fluid which is an agent for diluting blood and which contains a hyperosmotic agent to maintain the first fluid at an osmotic pressure of at least 285 mOsm;

(b) a second fluid that contains a surfactant and which is to be added to a sample of blood that has been diluted with the first fluid said surfactant selected from the group consisting of:

(i) a surfactant of a first group which is a polyoxyethylene-based anionic surfactant represented by the formula:

where $R_1$ is an alkyl, alkenyl, or alkynyl group having 10-22 carbon atoms;

$R_2$ is —O—,

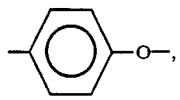

or COO;

n is an integer of 8-30

X is —$SO_3Na$, COONa, $OSO_3Na$ or ONa; and (ii) a surfactant of a second group which is a polyoxyethylene-based nonionic surfactant represented by the formula:

$R_1\text{-}R_1\text{-}(CH_2CH_2O)_n\text{-}H$ where
   $R_1$ is an alkyl, alkenyl, or alkynyl group having 10–22 carbon atoms;
   $R_2$ is —O—,

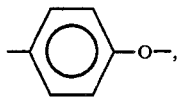

or COO;
   n is an integer of 8–30;
(c) a solubilizing agent that selectively reduces the size of monocytes in leukocytes.

2. A reagent for classifying leukocytes in a blood sample that lyses erythrocytes and which acts on leukocytes to enable the classification and counting of leukocytes, said reagent consisting essentially of a solubilizing agent that selectively reduces the size of monocytes in leukocytes and at least one surfactant selected from the group consisting of:
(a) a surfactant of a first group which is a polyoxyethylene-based anionic surfactant represented by the formula:

$R_1\text{-}R_2\text{-}(CH_2CH_2O)_n\text{-}X$ where
   $R_1$ is an alkyl, alkenyl or alkynyl group having 10–22 carbon atoms;
   $R_2$ is —O—,

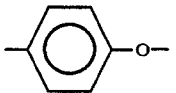

or COO;
   n is an integer of 8–30;
   X is $SO_3Na$, $COONa$, $OSO_3Na$ or $ONa$; and
(b) a surfactant of a second group which is a polyoxyethylene-based nonionic surfactant represented by the formula:

$R_1\text{-}R_2\text{-}(CH_2CH_2O)_n\text{-}H$ where
   $R_1$ is an alkyl, alkenyl or alkynyl group having 10–22 carbon atoms;
   $R_2$ is —O—,

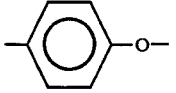

or COO;
   n is an integer of 8–30.

3. The reagent set forth in claim 1 which also contains a surfactant in the first fluid.

4. A method of detecting abnormal cells by the Radio Frequency and Direct Current particle analyzing methods using a reagent set forth in claim 1 or 2.

5. A method of classifying leukocytes into three types, lymphocytes, monocytes and granulocytes, and detecting abnormal cells by the Radio Frequency and Direct Current particle analyzing methods using a reagent set forth in claim 1 or 2.

6. A reagent for classifying leukocytes which is composed of the following two fluids (a) and (b):
(a) a first fluid which is a blood diluent and which contains a hyperosmotic agent; and
(b) a second fluid that contains the reagent set forth in claim 2 and which is to be added to a blood sample that has been diluted with the first fluid.

7. The reagent of claim 6 which also contains a surfactant in the first fluid.

8. The reagent of claim 2 which also contains a hyperosmotic agent.

9. A method of classifying leukocytes into lymphocytes, monocytes, and granulocytes by (a) detecting the change in electrical impedance at high frequency (Radio Frequency method) or by (b) detecting the change in current due to the differences in conductivity between suspended particles and a fluid medium in which they are suspended (Direct Current method) using the reagent as in any one of claims 2, 6, 7 or 8.

10. A method of classifying leukocytes into lymphocytes,.monocytes, and granulocytes by (1) detecting the change in electrical impedance at high frequency (Radio Frequency method) or by (2) detecting the change in current due to the differences in conductivity between suspended particles and a fluid medium in which they are suspended (Direct Current method) using the reagent of claim 1.

11. A method of classifying leukocytes into four types, lymphocytes, monocytes, eosinophils and granulocytes other than eosinophils, which comprises
(a) classifying the leukocytes in a blood sample into three types, lymphocytes, monocytes and granulocytes, by the method set forth in claim 9, and
(b) counting by both the Radio Frequency and Direct Current methods or by the Direct Current method alone eosinophils that selectively remain intact after the passage of a predetermined period of time in the sample that has been used for classification into three types.

12. A method of classifying leukocytes into four types, lymphocytes, monocytes, eosinophils and granulocytes other than eosinophils, which comprises
(a) classifying the leukocytes in a blood sample into three types, lymphocytes, monocytes and granulocytes, by the method set forth in claim 9, and
(b) counting by both the Radio Frequency and Direct Current methods or by the Direct Current method alone eosinophils that are selectively left intact in another portion of the same blood sample by using a reagent.

13. A method of classifying leukocytes into five types, lymphocytes, monocytes, eosinophils, basophils and neutrophils, which comprises
(a) classifying the leukocytes into four types, lymphocytes, monocytes, eosinophils and granulocytes other than eosinophils, by the method set forth in claim 11 and
(b) counting by both the Radio Frequency and Direct Current methods or by the Direct Current method alone basophils that are selectively left intact in another portion of the same blood sample by using a reagent for the measurement of basophils.

14. A reagent for enabling leukocytes in a blood sample to be classified and measured by lysing erythrocytes and protecting leukocyte membranes consisting essentially of a first cytolytic solution, having a pH of 1.5–5.0, an osmolarity of 10–120 mOsm/kg and containing a surfactant in an amount effective to reduce erythrocyte ghosts for distinction from leukocytes without causing undesirable leukocyte damage, said surfactant consisting essentially of a polyoxyethylene based nonionic surfactant represented by the general formula:

$R_1\text{-}R_2\text{-}(CH_2CH_2O)_n\text{-}H$ where $R_1$ is an alkyl, alkenyl or alkynyl group having 12–22 carbon atoms;

$R_2$ is —O—,

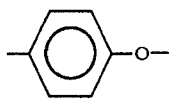

or —COO—; and n is an integer of 20–100.

15. A reagent as recited in claim 14, further consisting essentially of a second cytolytic solution combined with the first cytolytic solution, said reagent having a pH of 5.0–12.0, an osmolarity of 150–2000 mOsm/kg.

16. The reagent according to claim 15 wherein the second solution contains an additional amount of said polyoxyethylene based nonionic surfactant effective to further improve separation of lymphocytes, monocytes and granulocytes represented by the general formula:

$R_1\text{-}R_2\text{-}(CH_2CH_2O)_n\text{-}H$ where $R_1$ is an alkyl, alkenyl or alkynyl group having 12–22 carbon atoms;

$R_2$ is —O—,

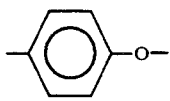

or —COO—; and n is an integer of 20–100.

17. A method of classifying leukocytes into four types, lymphocytes, monocytes, eosinophils and granulocytes other than eosinophils, which comprises:

(a) classifying the leukocytes in a blood sample into three types, lymphocytes, monocytes and granulocytes, by the method set forth in claim 10, and (b) counting by both the Radio Frequency and Direct Current methods or by the Direct Current method alone eosinophils that selectively remain intact after the passage of a predetermined period of time in the sample that has been used for classification into three types.

18. A method of classifying leukocytes into four types, lymphocytes, monocytes, eosinophils and granulocytes other than eosinophils, which comprises:

(a) classifying the leukocytes in a blood sample into three types, lymphocytes, monocytes and granulocytes, by the method set forth in claim 10, and (b) counting by the Radio Frequency and Direct Current methods or by the Direct Current method alone eosinophils that are selectively left intact in another portion of the same blood sample by using a reagent.

19. A method of classifying leukocytes into five types, lymphocytes, monocytes, eosinophils, basophils and neutrophils, which comprises:

(a) classifying the leukocytes into four types, lymphocytes, monocytes, eosinophils and granulocytes other than eosinophils, by the method set forth in claim 12 and (b) counting by both the Radio Frequency and Direct current methods or by the Direct Current method alone basophils that are selectively left intact in another portion of the same blood sample by using a reagent for the measurement of basophils.

20. A method of classifying leukocytes into five types, lymphocytes, monocytes, eosinophils, basophils and neutrophils, which comprises:

(a) classifying the leukocytes into four types, lymphocytes, monocytes, eosinophils and granulocytes other than eosinophils, by the method set forth in claim 17, and (b) counting by both the Radio Frequency and Direct current methods or by the Direct Current method alone basophils that are selectively left intact in another portion of the same blood sample by using a reagent for the measurement of basophils.

21. A method of classifying leukocytes into five types, lymphocytes, monocytes, eosinophils, basophils and neutrophils, which comprises:

(a) classifying the leukocytes into four types, lymphocytes, monocytes, eosinophils and granulocytes other than eosinophils, by the method set forth in claim 18, and (b) counting by both the Radio Frequency and Direct current methods or by the Direct Current method alone basophils that are selectively left intact in another portion of the same blood sample by using a reagent for the measurement of basophils.

22. The reagent according to claim 15 wherein the second cytolytic solution contains at least one additive for improving the separation of leukocytes during classification and measurement, said at least one additive being selected from the group consisting of:

urea
thiourea
1, 1-dimethylurea
ethyleneurea
methylurethane
1, 3-dimethylurea
urethane ($H_2NCOOC_2H_5$)
N-octyl B-D-glucoside
CHAPS (3-{(3-chloroamidopropy)dimethylammonio}-1-propanesullfonate)
CHAPSO (3-{(3-chloroamidopropyl) dimethylammonio}-2-hydroxy-1-propanesulfonate)
MEGA 8,9,10 (octanoyl-, nonanoyl- or decanoyl-N-methylglucamide)
sucrose monocaprate
N-formylmethylleucylalanine
guanidine thiocyanate
guanylguanidine
guanidine chloride
guanidine rhodanate
guanidine nitrate
1,1,3,3-tetraguanidine
guanidine carbonate
guanidine phosphate
guanidine sulfate
sodium deoxycholate
taurocholic acid
cholic acid
sodium trichloroacetate
sodium tribromoacetate sodium dichloroacetate
sodium dibromoacetate
sodium monochloroacetate and
sodium monobromoacetate.

23. The reagent set forth in claim 1 or 2 wherein the contained solubilizing agent is at least one member selected from the group consisting of:
urea
thiourea
1,1-dimethylurea
ethyleneurea
methylurethane
1,3-dimethylurea
urethane ($H_2NCOOC_2H_5$)
N-octyl B-D-glucoside
CHAPS (3-{(3-chloroamidopropy)dimethylammonio}-1-propanesullfonate)
CHAPSO (3-{(3-chloroamidopropyl) dimethylammonio}-2-hydroxy-1-propanesulfonate)
MEGA 8,9,10 (octanoyl-, nonanoyl- or decanoyl-N-methylglucamide)
sucrose monocaprate
N-formylmethylleucylalanine
guanidine thiocyanate
guanylguanidine
guanidine chloride
guanidine rhodanate
guanidine nitrate
1,1,3,3-tetraguanidine
guanidine carbonate
guanidine phosphate
guanidine sulfate
sodium deoxycholate
taurocholic acid
cholic acid
sodium trichloroacetate
sodium tribromoacetate
sodium dichloroacetate
sodium dibromoacetate
sodium monochloroacetate, and
sodium monobromoacetate.

24. A method of classifying leukocytes according to claim 1 or 2 using a reagent that contains at least one of the solubilizing agents:
n-octyl-B-D-glucoside
CHAPS (3-{(3-chloramidopropyl)dimethylammonio}-1-propanesulfonate)
CHAPSO (3-{3-chloramidopropyl-dimethyl-ammonio}-2-hydroxy-1-propanesulfonate)
MEGA 8, 9, 10 (octanoyl-, nonanoyl- or decanoyl-N-methylglucamide)
sucrose monocaprate
N-formylmethylleucylalanine.

25. A method for classifying leukocytes into at least three types, including lymphocytes, monocytes and granulocytes, comprising the steps of:

(a) treating a blood sample with a reagent capable of lysing erythrocytes and protecting leukocyte membranes for subsequent classification, said reagent having a pH of 1.5-5.0, an osmolarity of 10-120 mOsm/kg, and containing a surfactant in an amount effective to reduce erythrocyte ghosts for distinction from leukocytes without causing undesirable leukocyte damage, said surfactant consisting essentially of a polyoxyethylene based nonionic surfactant represented by the formula:
$R_1$-$R_2$-$(CH_2CH_2O)_n$-H
where
$R_1$ is an alkyl, alkenyl or alkynyl group having 12-22 carbon atoms;
$R_2$ is —O—,

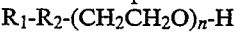

or —COO—; and
n is an integer in the range 20-100;
(b) measuring the DC volume and RF size to produce a scattergram; and
(c) observing populations of the at least three types of leukocytes.

26. A method for detecting abnormal leukocytes and nucleate erythrocytes, comprising the steps of:
(a) treating a blood sample with a reagent capable of lysing erythrocytes and protecting leukocyte membranes for subsequent classification, said reagent having a pH of 1.5-5.0, an osmolarity of 10-120 mOsm/kg, and containing a surfactant in an amount effective to reduce erythrocyte ghosts for distinction from leukocytes without causing undesirable leukocyte damage, said surfactant consisting essentially of a polyoxyethylene based nonionic surfactant represented by the formula:
$R_1$-$R_2$-$(CH_2CH_2O)_n$-H
where
$R_1$ is an alkyl, alkenyl or alkynyl group having 12-22 carbon atoms;
2 is —O—,

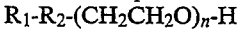

or —COO—; and
n is an integer in the range 20-100;
(b) measuring the DC volume and RF size to produce a scattergram; and
(c) observing populations of abnormal leukocytes and nucleate erythrocytes.

* * * * *

UNITED STATES PATENT AND TRADEMARK OFFICE
CERTIFICATE OF CORRECTION

PATENT NO. : 5,389,549
DATED : February 14, 1995
INVENTOR(S) : Hamaguchi et al.

Sheet 1 of 5

It is certified that error appears in the above-indentified patent and that said Letters Patent is hereby corrected as shown below:

Column 3, line 3, delete "vol 16 pp" and insert --vol. 16 , pp.--.

Column 3, line 12, delete "Testing)" and insert --Testing)",--.

Column 3, line 31, delete "Testing)" vol" and insert --Testing)", vol.--.

Column 3, line 32, delete "pp" and insert --pp.--.

Column 5, line 10, delete "On" and insert --on--.

Column 5, line 44, delete "No.." an insert --No.--.

Column 7, line 7, delete "(Rinsh6" and insert --(Rinshõ--.

UNITED STATES PATENT AND TRADEMARK OFFICE
CERTIFICATE OF CORRECTION

PATENT NO. : 5,389,549
DATED : February 14, 1995
INVENTOR(S) : Hamaguchi et al.

It is certified that error appears in the above-indentified patent and that said Letters Patent is hereby corrected as shown below:

Column 7, line 9, delete "3" and insert --3,--.

Column 9, line 50, delete "in".

Column 11, line 38, after "The" insert --second--.

Column 14, line 23, delete "a" and insert --$\underline{a}$--.

Column 14, line 23, delete "b" and insert --$\underline{b}$--.

Column 14, line 24, delete "c" and insert --$\underline{c}$--.

Column 14, line 24, delete "i" and insert --$\underline{i}$--.

Column 14, line 40, delete "a" and insert --$\underline{a}$--.

Column 14, line 41, delete "b" and insert --$\underline{b}$--.

UNITED STATES PATENT AND TRADEMARK OFFICE
CERTIFICATE OF CORRECTION

PATENT NO. : 5,389,549
DATED : February 14, 1995
INVENTOR(S) : Hamaguchi et al.

Sheet 3 of 5

It is certified that error appears in the above-indentified patent and that said Letters Patent is hereby corrected as shown below:

Column 14, line 41, delete "c" and insert --$\underline{c}$--.

Column 15, line 39, delete "j," and inset --$\underline{j}$,--.

Column 15, line 40, delete "k" and insert --$\underline{k}$--.

Column 15, line 40, delete "l" and insert --$\underline{l}$--.

Column 15, line 41, delete "m" and insert --$\underline{m}$--.

Column 15, line 41, delete "n" and insert --$\underline{n}$--.

Column 15, line 42, delete "o" and insert --$\underline{o}$--.

Column 15, line 43, delete "p" and insert --$\underline{p}$--.

Column 15, line 49, delete ".leukocytes" and insert --leukocytes--.

UNITED STATES PATENT AND TRADEMARK OFFICE
CERTIFICATE OF CORRECTION

PATENT NO. : 5,389,549

DATED : February 14, 1995

INVENTOR(S) : Hamaguchi et al.

Sheet 4 of 5

It is certified that error appears in the above-indentified patent and that said Letters Patent is hereby corrected as shown below:

Column 16, line 18, delete "4,409,917" and insert --4,099,917--.

Column 17, line 63, delete "Cell" and insert --cell--.

Column 24, line 1, delete "mOnocytes" and insert --monocytes--.

Column 24, line 60, delete "$(CH_2CH_2\text{--}O\text{--})_{23}$" and insert --$(CH_2CH_2O)_{23}$--.

Column 26, line 42, delete "a" and insert --$\underline{a}$--.

Column 26, line 43, delete "h" and insert --$\underline{b}$--.

Column 26, line 43, delete "c" and insert --$\underline{c}$--.

Column 27, line 3, delete "[Cl$_{18}$" and insert --[C$_{18}$--.

UNITED STATES PATENT AND TRADEMARK OFFICE
CERTIFICATE OF CORRECTION

PATENT NO. : 5,389,549
DATED : February 14, 1995
INVENTOR(S) : Hamaguchi et al.

It is certified that error appears in the above-indentified patent and that said Letters Patent is hereby corrected as shown below:

Column 27, line 31, delete "a" and insert --$\underline{a}$--.

Column 27, line 32, delete "b" and insert --$\underline{b}$--.

Column 27, line 32, delete "c" and insert --$\underline{c}$--.

Column 27, line 48, delete "Table 3" (second occurrence) and insert --Table 2--.

Column 31, line 32, delete "[CH$_3$(CH$_2$)T" and insert --[CH$_3$(CH$_2$)$_7$--.

Column 31, line 53, delete the carriage return after "after".

Column 32, line 27, after "detected." start a new paragraph.

Column 34, line 23, delete "phocytes,.monocytes" and insert --phocytes, monocytes--.

Signed and Sealed this

Second Day of January, 1996

BRUCE LEHMAN

*Attest:*

*Attesting Officer*          *Commissioner of Patents and Trademarks*